US009611294B2

(12) United States Patent
Cardozo et al.

(10) Patent No.: US 9,611,294 B2
(45) Date of Patent: Apr. 4, 2017

(54) PEPTIDES MIMICKING HIV-1 VIRAL EPITOPES IN THE V2 LOOP FOR THE GP120 SURFACE ENVELOPE GLYCOPROTEIN

(75) Inventors: Timothy Cardozo, New York, NY (US); Xiangpeng Kong, New York, NY (US); Susan Zolla-Pazner, New York, NY (US)

(73) Assignee: New York University, New York, NY (US)

( * ) Notice: Subject to any disclaimer, the term of this patent is extended or adjusted under 35 U.S.C. 154(b) by 352 days.

(21) Appl. No.: 13/612,300

(22) Filed: Sep. 12, 2012

(65) Prior Publication Data

US 2013/0071424 A1    Mar. 21, 2013

Related U.S. Application Data

(60) Provisional application No. 61/533,424, filed on Sep. 12, 2011.

(51) Int. Cl.

| | |
|---|---|
| *C07K 7/64* | (2006.01) |
| *A61K 38/19* | (2006.01) |
| *A61K 39/21* | (2006.01) |
| *A61K 39/12* | (2006.01) |
| *C07K 7/08* | (2006.01) |
| *C07K 14/005* | (2006.01) |
| *C07K 14/245* | (2006.01) |
| *C07K 16/10* | (2006.01) |
| *C07K 14/28* | (2006.01) |
| *G01N 33/68* | (2006.01) |
| *G01N 33/569* | (2006.01) |
| *A61K 39/00* | (2006.01) |

(52) U.S. Cl.
CPC .............. *C07K 7/08* (2013.01); *A61K 38/19* (2013.01); *A61K 39/12* (2013.01); *A61K 39/21* (2013.01); *C07K 7/64* (2013.01); *C07K 14/005* (2013.01); *C07K 14/245* (2013.01); *C07K 14/28* (2013.01); *C07K 16/1063* (2013.01); *G01N 33/56988* (2013.01); *G01N 33/6854* (2013.01); *A61K 2039/545* (2013.01); *A61K 2039/6037* (2013.01); *A61K 2039/64* (2013.01); *C07K 2317/34* (2013.01); *C07K 2317/76* (2013.01); *C07K 2319/55* (2013.01); *C12N 2740/16122* (2013.01); *C12N 2740/16134* (2013.01); *C12N 2799/023* (2013.01); *G01N 2333/162* (2013.01); *G01N 2469/20* (2013.01)

(58) Field of Classification Search
CPC .............. C07K 2319/00; C07K 14/005; C07K 16/1063; C07K 1/047; C07K 2317/76; C07K 2319/55; C07K 7/08; C07K 7/64; A61K 38/00; A61K 2039/6037; A61K 2039/64; A61K 35/12; A61K 38/19; A61K 47/42; C12N 2740/16122; C12N 2740/16134

See application file for complete search history.

(56) References Cited

U.S. PATENT DOCUMENTS

| 6,042,836 A | 3/2000 | Berman et al. |
|---|---|---|
| 2003/0105282 A1 | 6/2003 | Pinter |
| 2009/0098144 A1 | 4/2009 | Zolla-Pazner et al. |

FOREIGN PATENT DOCUMENTS

| RU | 2237065 C2 | | 9/2004 |
|---|---|---|---|
| RU | 2312941 C2 | | 12/2007 |
| WO | WO 99/12556 | * | 3/1999 |
| WO | WO 99/16466 | * | 4/1999 |
| WO | WO 2008/010930 | * | 1/2008 |
| WO | WO 2013/085550 | * | 6/2013 |

OTHER PUBLICATIONS

Matthews et al., 1987, AIDS Research and Human Retroviruses, 3(1):197-206.*
Burton and Moore, Nature Medicine, 1998, 4(5):495-498.*
Desrosiers, Nature Medicine, 2004, 10(3):221-223.*
Shotton et al., Journal of Virology, 1995, 69(1):222-230.*
Yang et al., Journal of Virology, 2001, 75(3):1165-1171.*
Walker et al., Science, Oct. 9, 2009; 326(5950):285-289.*
Carlos et al., "Immunogenicity of a Vaccine Preparation Representing the Variable Regions of the HIV Type 1 Envelope Glycoprotein," AIDS Res. Hum. Retroviruses 16(2):153-61 (2000).
McKenzie et al., "Cholera Toxin B Subunit as a Carrier Protein to Stimulate a Mucosal Immune Response," J. Immunol. 133(4):1818-24 (1984).
International Search Report and Written Opinion for PCT/US2012/054871 dated Dec. 27, 2012.

* cited by examiner

*Primary Examiner* — Nicole Kinsey White
(74) *Attorney, Agent, or Firm* — LeClairRyan, a Professional Corporation

(57) ABSTRACT

The present invention relates to an isolated immunogenic peptide comprising a V2 loop fragment from HIV surface envelope glycoprotein gp120. This peptide binds specifically with antibodies in blood of patients vaccinated with a vaccine that has shown protection from HIV-1 infection, does not react with blood of matched patients who did not receive the vaccine, and can, therefore, elicit anti-HIV-1 antibodies which protect against HIV-1 infection. Other aspects of the present invention relate to an isolated immunogenic polypeptide comprising the peptide inserted into an immunogenic scaffold protein, a vaccine composition comprised of the immunogenic peptide and an immunologically or pharmaceutically acceptable vehicle or excipient as well as methods of inducing an immune response against HIV-1 and methods of detecting HIV-1.

11 Claims, 8 Drawing Sheets

PEPTIDES MIMICKING HIV-1 VIRAL EPITOPES IN THE V2 LOOP FOR THE GP120 SURFACE ENVELOPE GLYCOPROTEIN

This application claims the benefit of U.S. Provisional Patent Application Ser. No. 61/533,424, filed Sep. 12, 2011, which is hereby incorporated by reference in its entirety.

The subject matter of this application was made with support from the United States National Institutes of Health Grant No. R01-AI084119. The U.S. government has certain rights in the invention.

FIELD OF THE INVENTION

The present invention relates to a peptide mimicking HIV-1 viral epitopes in the V2 loop for the gp120 surface envelope glycoprotein.

BACKGROUND OF THE INVENTION

Human Immunodeficiency Virus-1 (HIV-1) infection has been reported throughout the world in both developed and developing countries. HIV-2 infection is found predominately in West Africa, Portugal, and Brazil. At the end of 2008, an estimated 1,178,350 persons aged 13 and older were living with HIV infection in the United States. Of those, 20% had undiagnosed HIV infections (CDC, "HIV Surveillance—United States, 1981-2008," *MMWR* 60(21); 689-693 (2008), which is hereby incorporated by reference in its entirety).

The HIV viruses are members of the Retroviridae family and, more particularly, are classified within the Lentivirinae subfamily. Like nearly all other viruses, the replication cycles of members of the Retroviridae family, commonly known as the retroviruses, include attachment to specific cell receptors, entry into cells, synthesis of proteins and nucleic acids, assembly of progeny virus particles (virions), and release of progeny viruses from the cells. A unique aspect of retrovirus replication is the conversion of the single-stranded RNA genome into a double-stranded DNA molecule that must integrate into the genome of the host cell prior to the synthesis of viral proteins and nucleic acids.

HIV encodes a number of genes including three structural genes—gag, pol, and env—that are common to all retroviruses. The envelope protein of HIV-1 is a glycoprotein of about 160 kd (gp160). During virus infection of the host cell, gp160 is cleaved by host cell proteases to form gp120 and the integral membrane protein, gp41. The gp41 portion is anchored in the membrane bilayer of virion, while the gp120 segment protrudes into the surrounding environment. gp120 and gp41 are more covalently associated, and free gp120 can be released from the surface of virions and infected cells. The gp120 polypeptide is also instrumental in mediating entry into the host cell.

Historically, viral vaccines have been enormously successful in the prevention of infection by a particular virus. Therefore, when HIV was first isolated, there was a great amount of optimism that an HIV vaccine would be developed quickly. However, this optimism quickly faded, because a number of unforeseen problems emerged.

It is widely thought that a successful vaccine should be able to induce a strong, broadly neutralizing antibody response against diverse HIV-1. Neutralizing antibodies, by attaching to the incoming virions, can reduce or even prevent their infectivity for target cells and prevent the cell-to-cell spread of virus in tissue. Conventional wisdom suggests that "constant" rather than "variable" regions of Env would induce the most broadly reactive antibodies. The failure of the Vaxgen HIV vaccine trial demonstrated that the sequence-conserved regions of HIV gp120 do not induce protective neutralizing antibodies, since these regions were present in the gp120 immunogen used in that study. The failure of the STEPS HIV vaccine demonstrated that cellular immunity utilizing non-Env determinants is not protective. Thus, one could conclude that targeting the sequence-conserved (including non-Env and the core of Env) regions of the HIV-1 virus for protective immunity will not work. Thus, there remains a need for envelope antigens that can elicit an immunological response in a subject against multiple HIV strains and subtypes, for example when administered as a vaccine.

The present invention is directed to overcoming deficiencies of prior approaches to addressing HIV infection.

SUMMARY OF THE INVENTION

The present invention relates to an isolated immunogenic peptide comprising a V2 loop fragment from HIV surface envelope glycoprotein gp120. This peptide binds specifically with antibodies in blood of patients vaccinated with a vaccine that has shown protection from HIV-1 infection, does not react with blood of matched patients who did not receive the vaccine, and can, therefore, elicit anti-HIV-1 antibodies which protect against HIV-1 infection.

Other aspects of the present invention relate to an isolated immunogenic polypeptide comprising the peptide inserted into an immunogenic scaffold protein, a vaccine composition comprised of the immunogenic peptide and an immunologically or pharmaceutically acceptable vehicle or excipient as well as methods of inducing an immune response against HIV-1 and methods of detecting HIV-1.

The RV144 HIV-1 vaccine trial was the first to demonstrate evidence of protection against HIV-1 infection, with an estimated vaccine efficacy of 31.2% (Rerks-Ngarm et al., "Vaccination with ALVAC and AIDSVAX to Prevent HIV-1 Infection in Thailand," *N Engl J Med.* 361:2209-2220 (2009), which is hereby incorporated by reference in its entirety). This vaccine consisted of four doses of a recombinant canary pox priming immunogen, ALVAC-HIV (vCP1521), and two doses of AIDSVAX® B/E, recombinant HIV-1 gp120 proteins from HIV-1 subtype B and circulating recombinant form 01_AE (CRF01_AE).

In order to identify correlates of risk of HIV-1 infection in RV144, two sequential sets of analyses of plasma specimens from study participants were conducted (Haynes et al., "Immune Correlates Analysis of the ALVAC-AIDSVAX HIV-1 Vaccine Efficacy Trial," *N Engl J Med.* 366:1275-1286 (2012), which is hereby incorporated by reference in its entirety). The first was a series of pilot studies in which 32 types of immunologic assays were performed on sets of plasma and peripheral blood mononuclear cells from uninfected participants who had received either the placebo or the vaccine. Results from the pilot studies were used to select assays for the subsequent case-control study of immune correlates of infection risk. Assays for the case-control study were chosen if the results in the pilot studies showed low false positive rates, a broad dynamic range, low background reactivity, and low specimen volume requirements (Haynes et al., "Immune Correlates Analysis of the ALVAC-AIDSVAX HIV-1 Vaccine Efficacy Trial," *N Engl J Med.* 366:1275-1286 (2012), which is hereby incorporated by reference in its entirety). Seventeen assay types were selected for the case-control study, and these generated results for 158 variables. To preserve maximal statistical power, six were chosen as primary variables in the case-control study and were analyzed by multivariate analysis. To expand the search for immune correlates, all 158 variables were subsequently evaluated by univariate analyses.

Case-control specimens consisted of specimens drawn two weeks after the last immunization from 41 infected vaccines (cases) and from 205 matched uninfected vaccines (controls). Two of the six primary variables significantly correlated with HIV-1 infection risk in vaccine recipients: 1) the level of plasma IgG antibodies reactive with gp70-V1V2, a scaffolded protein carrying the first and second variable regions of the HIV-1 gp120 envelope glycoprotein fused to murine leukemia virus gp70. Levels of antibodies specific for gp70-V1V2 were correlated inversely with the risk of infection; 2) the level of plasma IgA antibodies reactive with a panel of 14 envelope glycoproteins correlated directly with risk of infection.

The participation of the V2 region of gp120 in the infectious process, and the role of V2 specific antibodies in protection from infection has been the subject of investigation and controversy for nearly two decades. Although, by definition, "variable" regions—like V2—vary in amino acid sequence, many residues in these regions do not vary, or tolerate only conservative changes (Zolla-Pazner et al, "Structure-Function Relationships of HIV-1 Envelope Sequence-Variable Regions Provide a Paradigm for Vaccine Design," *Nat Rev Immunol* 10: 527-535 (2010), which is hereby incorporated by reference in its entirety). These conserved amino acids can form structural elements that result in immunologic cross-reactivity between diverse viruses; for example many V2- and V3-specific antibodies are highly cross-reactive with diverse HIV-1 envelopes (Gorey et al., "Repertoire of Neutralizing Human Monoclonal Antibodies Specific For the V3 Domain of HIV-1 gp120," *J Immunol.* 150: 635-643 (1993); Israel et al., "Prevalence of a V2 Epitope in Clade B Primary Isolates and its Recognition by Sera from HIV-1 Infected Individuals," *Aids* 11: 128-130 (1997); Krachmarov et al., "Antibodies That are Cross-Reactive for Human Immunodeficiency Virus Type 1 Clade A and Clade B V3 Domains are Common in Patient Sera From Cameroon, but Their Neutralization Activity is Usually Restricted by Epitope Masking," *J. Virol.* 79: 780-790 (2005); Gorey et al., "Functional and Immunochemical Cross-Reactivity of V2-Specific Monoclonal Antibodies From Human Immunodeficiency Virus Type 1-Infected Individuals," *Virology* 427: 198-207 (2012); Nyambi et al., "Immunoreactivity of Intact Virions of Human Immunodeficiency Virus Type 1 (HIV-1) Reveals the Existence of Fewer HIV-1 Immunotypes Than Genotypes," *J Virol* 74: 10670-10680 (2000); Hioe et al., "Anti-V3 Monoclonal Antibodies Display Broad Neutralizing Activities Against Multiple HIV-1 Subtypes," *PLoS ONE* 5: e10254 (2010), each of which is hereby incorporated by reference in its entirety). Moreover, the conserved structural features are required for these regions to perform important biologic functions. Thus, for example, conserved elements within V2 participate in the formation of the bridging sheet (a constituent of the chemokine receptor binding site (Thali et al., "Characterization of Conserved HIV-type 1 gp120 Neutralization Epitopes Exposed Upon gp120-CD4 Binding," *J Virol* 67: 3978-3988 (1993); Rizzuto et al., "A Conserved HIV gp120 Glycoprotein Structure Involved in Chemokine Receptor Binding," *Science* 280: 1949-1953 (1998); Kwong et al. "Structure of an HIV gp120 Envelope Glycoprotein in Complex With the CD4 Receptor and a Neutralizing Human Antibody," *Nature* 393: 648-659 (1998), each of which is hereby incorporated by reference in its entirety), and V2 contains a tripeptide motif in the mid-loop region of V2 that is a putative α4β7 integrin binding site (Arthos et al., "HIV-1 Envelope Protein Binds to and Signals Through Iintegrin alpha4beta7, the Gut Mucosal Homing Receptor for Peripheral T cells," *Nat Immunol* 9: 301-309 (2008), which is hereby incorporated by reference in its entirety). Similarly, conserved elements of V3 contribute to its role in binding to the chemokine receptor (Trkola et al., "CD4-Dependent, Antibody-Sensitive Interactions Between HIV-1 and its Co-Receptor CCR-5," *Nature* 384: 184-187 (1996); Hill et al., "Envelope Glycoproteins From HIV-1, HIV-2 and SIV Can Use Human CCR5 as a Coreceptor for Viral Entry and Make Direct CD4-Dependent Interactions With This Chemokine Receptor," *J Virol* 71: 6296-6304 (1997), each of which is hereby incorporated by reference in its entirety).

Antibodies specific for V2 occur in only ~25-40% of HIV-infected individuals (Israel et al., "Prevalence of a V2 Epitope in Clade B Primary Isolates and its Recognition by Sera from HIV-1 Infected Individuals," *Aids* 11: 128-130 (1997); Kayman et al., "Presentation of Native Epitopes in the V1/V2 and V3 Regions of Human Immunodeficiency Virus Type 1 gp120 by Fusion Glycoproteins Containing Isolated gp120 Domains," *J. Virol.* 68: 400-410 (1994), each of which is hereby incorporated by reference in its entirety). Interestingly, the cross-reactivity of these antibodies does not require extensive mutation from the VH germ line since V2-specific monoclonal antibodies from HIV-infected individuals display a mean 6.2% mutation frequency from germ line (Gorny et al., "Functional and Immunochemical Cross-Reactivity of V2-Specific Monoclonal Antibodies From Human Immunodeficiency Virus Type 1-Infected Individuals," *Virology* 427: 198-207 (2012), which is hereby incorporated by reference in its entirety) which is comparable to a mean 6.8% mutation frequency found in Abs from normal individuals (Tiller et al., "Autoreactivity in Human IgG+ Memory B Cells," *Immunity* 26: 205-213 (2007), which is hereby incorporated by reference in its entirety). Thus, because a large body of data suggests that V2 may be a site of HIV-1 vulnerability, and because a strong antibody response to gp70-V1V2 was correlated with reduced infection in the RV144 clinical vaccine trial, a thorough analysis of all V2 antibody assays used in the RV144 immune correlates study was undertaken, as disclosed here.

BRIEF DESCRIPTION OF THE DRAWINGS

FIG. 5A shows four 21-mer N-terminal biotinylated peptides (Peptides 1-4 (SEQ ID NOS: 3 to 6)) were selected on the basis of a bioinformatics analysis of V2 sequences from the LANL HIV Database. FIG. 5B shows a second peptide panel designed upon inspection of the amino acids in Peptides 1-4 (SEQ ID NOS: 3 to 6) in FIG. 5A revealed amino acids that distinguish Peptides 1 (SEQ ID NO: 3) and 3 (SEQ ID NO: 5) from 2 (SEQ ID NO: 4) and 4 (SEQ ID NO: 6); these appear at positions 165, 169, 172, and 174. To maximally enhance the availability of the epitopes on the peptides used in the fine mapping of the V2 antibodies, a spacer of three glycines was inserted between the biotin tag at the N-terminus of the peptide and the V2 sequences.

FIG. 8A shows an aggregate response across all sub-types averaged across vaccines as a function of HxB2 positions. An individual aggregate response is computed using a sliding window mean statistic of 9 amino acids, i.e., peptides with HxB2 positions of 9 contiguous amino acids averaged together. In FIG. 8B, the actual sequence of each of the overlapping 15-mers (SEQ ID NOS: 17 to 65) spanning V2 positions 160-183 is shown. The seven sets of peptides represent the consensus V2 regions of HIV-1 Group M and of subtypes A, B, C, D, CRF01_AE and CRF02_AG. Peptides are shaded according to their average response across all vaccines, with a scale of 0 (white) to 1.8 (black). The V2 sequence of HxB2 is shown above the graph with the corresponding HxB2 numbering, and this numbering is also shown on the x-axis. The bold arrow indicates that the estimated aggregate response is highest when centered at position 173, though peptides centered on position 170, i.e., with the V2 peptide spanning residues 163-177 have the highest response. All responses are calculated using normalized intensities and by subtracting the intensities of baseline pre-bleeds.

DETAILED DESCRIPTION OF THE INVENTION

Figure 1:
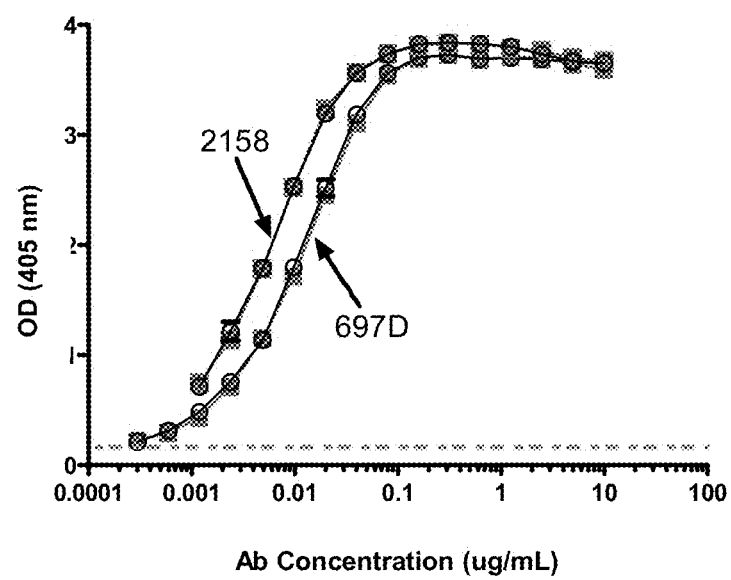
FIG. 1 shows the ELISA reactivity of human anti-V2 monoclonal antibodies 697-D and 2158 with AIDSVAX subtype E and AIDSVAX subtype B gp120 immunogens. The dashed line represents twice background levels.

The present invention relates to an isolated immunogenic peptide comprising a V2 loop fragment from HIV surface envelope glycoprotein gp120. This peptide binds specifically with antibodies in blood of patients vaccinated with a vaccine that has shown protection from HIV-1 infection, does not react with blood of matched patients who did not receive the vaccine, and can, therefore, elicit anti-HIV-1 antibodies which protect against HIV-1 infection.

In accordance with this aspect of the present invention, suitable isolated immunogenic peptides include peptides of the amino acid sequence $X_1X_2DX_3X_4X_5X_6X_7YX_8X_9X_{10}X_{11}X_{12}$ (SEQ ID NO: 1), where $X_1$ is L, V, I, M, F, W or A; $X_2$ is any amino acid; $X_3$ is R, K or H; $X_4$ is K, D, E, R, H, S, T, C, N, Q, Y, A, V or M; $X_5$ is K, D, E, R, H, S, T, C, N, Q, Y or A; $X_6$ is K, D, E, R, H, S, T, C, N, Q, Y or A; $X_7$ is L, V, I, M, F, W, A or E; $X_8$ is K, D, E, R, H, S, T, C, N, Q, Y or A; $X_9$ is L, V, I, M, F, W or A; $X_{10}$ is F or T, $X_{11}$ is K, D, E, R, H, S, T, C, N, Q, Y or A; $X_{12}$ is K, D, E, R, H, S, T, C, N, Q, Y or A. Examples of specific immunogenic peptides in accordance with the present invention include the following amino acid sequences: LRDKKQRVYSLFYK (SEQ ID NO: 7), IRDKKQRVYSLFYK (SEQ ID NO: 11), LRDKVQRVYSLFYK (SEQ ID NO: 12), LRDKKQREYSLFYK (SEQ ID NO: 13), LRDKKQRVYALFYK (SEQ ID NO: 14), or LQNKKQQVYSLFYQ (SEQ ID NO: 15).

Another aspect of the present invention is an isolated immunogenic peptide including the amino acid sequence of SEQ ID NO: 2. In accordance with this aspect of the present invention, suitable isolated immunogenic peptides include peptides of the amino acid sequence of SEQ ID NO:1 with $X_{11}$ as any amino acid other than Y. In particular, SEQ ID NO: 2 has the following amino acid sequence: $X_1X_2DX_3X_4X_5X_6X_7YX_8X_9X_{10}X_{11}X_{12}$, where $X_1$ is L, V, I, M, F, W or A; $X_2$ is any amino acid; $X_3$ is R, K or H; $X_4$ is K, D, E, R, H, S, T, C, N, Q, Y, A, V or M; $X_5$ is K, D, E, R, H, S, T, C, N, Q, Y or A; $X_6$ is K, D, E, R, H, S, T, C, N, Q, Y or A; $X_7$ is L, V, I, M, F, W, A or E; $X_8$ is K, D, E, R, H, S, T, C, N, Q, Y or A; $X_9$ is L, V, I, M, F, W or A; $X_{10}$ is F or T, $X_{11}$ is any amino acid other than Y; $X_{12}$ is K, D, E, R, H, S, T, C, N, Q, Y or A.

In another aspect of the present invention, the isolated immunogenic peptide comprises the amino acid sequence of LRDKMQKVYALTYK (SEQ ID NO: 16). This is a sequence that does not occur in nature and has a mutation, relative to the amino acid sequence of SEQ ID: 1, which requires Y at position $X_{11}$. This destroys a cathepsin protease cleavage site.

The present invention also relates to an isolated immunogenic polypeptide of the present invention comprising the isolated immunogenic peptide described above and an immunogenic scaffold protein. The polypeptide has a conformation that is recognized by, and bound by, a broadly neutralizing anti-HIV-1 antibody.

As used herein, a "broadly neutralizing" antibody or antibody response is an antibody or response that results in binding and neutralization of at least one group of heterologous HIV-1 viruses that are members of a different subtype or clade than that of the source of the immunizing antigen. The scaffold protein can be one that is highly immunogenic and capable of enhancing the immunogenicity of any heterologous sequences fused to/inserted in it. Suitable scaffold proteins include, without limitation, a cholera toxin and an enterotoxin.

In one embodiment of the present invention, the scaffold protein is cholera toxin subunit B (CTB). CTB is highly immunogenic and has been used in fusion constructs to enhance immunogenicity of its fusion partner polypeptide or peptide (McKenzie et al., "Cholera Toxin B Subunit as a Carrier to Stimulate a Mucosal Immune Response," *J Immunol.* 133:1818-1824 (1984); Czerkinsky et al., "Oral Administration of a Streptococcal Antigen Coupled to Cholera Toxin B Subunit Evokes Strong Antibody Responses in Salivary Glands and Extramucosal Tissues," *Infect Immun.* 57:1072-1077 (1989), each of which is hereby incorporated by reference in its entirety). CTB has also been described as a mucosal adjuvant for vaccines (Areas et al., "Expression and Characterization of Cholera Toxin B-Pneumococcal Surface Adhesin A Fusion Protein in *Escherichia Coli*: Ability of CTB-PsaA to Induce Humoral Immune Response in Mice," *Biochem Biophys Res Commun.* 321:192-196 (2004), which is hereby incorporated by reference in its entirety).

In another embodiment of the present invention, the scaffold protein is an *E. coli* enterotoxin, preferably heat labile entertoxin. This protein is also highly immunogenic and has been used in fusion constructs to enhance immunogenicity of its fusion partner polypeptide or peptide (Lipscombe et al., "Intranasal Immunization Using the B Subunit of the *Escherichia Coli* Heat Labile Toxin Fused to an Epitope of the *Bordetella Pertussis* P.69 Antigen," *Mol. Microbiol.* 5:1385-1392 (1991), which is hereby incorporated by reference in its entirety).

An important factor for the immunogenic property of CTB and heat labile enterotoxin is their binding to GM1 ganglioside, which is present on the surface of mucosal cells. This results in its propensity to induce mucosal immunity and is highly desirable for an HIV immunogen or vaccine, because infection commonly occurs via a mucosal route. In addition, the availability of structural information of these proteins allows protein design that avoids or minimizes disruption of the GM1 binding site, thereby preserving the inherent immunogenicity of these polypeptides.

In accordance with this aspect of the present invention, the immunogenic peptide can be inserted directly into the scaffold's tertiary structure. This yields a polypeptide in which an exceptionally high fraction of the molecular surface presents V2 epitopes that are recognized by broadly-reactive neutralizing anti-gp120 antibodies and can elicit anti-HIV-1 antibody responses that preferably are broadly-reactive and neutralize the virus. Molecular modeling is used to test in-silico, whether various insertion positions in the scaffold and different loop lengths result in loop conformations that present the epitopes. Specifically, there are two approaches. Firstly, the scaffold is scanned for amino-acid positions that can be superimposed on the termini of the loop as observed in the V2/antibody complex. When superposition within small tolerances (<0.5 .ANG. root mean square deviation (RMSD) for the terminal residues is achieved, the model is evaluated for the absence of clashes with the scaffold structure. Secondly, the loop is inserted in a random conformation and subjected to conformational sampling. Low energy conformations generated during sampling are compared to the desired V2 conformation as observed in the V2/antibody complex. Sampling is over a restricted energy range. When the construct is such that conformations within 1.0 .ANG. backbone RMSD of the desired V2 conformation are identified in the simulation, a model of the immunogen-antibody complex is built to ensure that the scaffold does not interfere with the V2 loop/antibody binding.

The isolated immunogenic peptides described above may also exist in a cyclized form. These cyclic peptides can be synthesized and include two cysteine residues that bond via a disulfide linkage forming the cyclic peptide. Alternatively, the peptide may be cyclized by chemical means without relying upon disulfide bonding of two cysteine residues, for example, by introduction of a linker.

The cyclic peptide compositions of the present invention may be synthesized using ordinary skill in the art of organic synthesis and peptide synthesis. Methods for restricting the secondary structure of peptides and proteins are highly desirable for the rational design of therapeutically useful conformationally-restricted (or "locked") pharmacophores. The purely chemical approaches for restricting secondary structure often require extensive multistep syntheses (Olson, G. L., *J. Am. Chem. Soc.* 112:323 (1990)). An alternative approach involves installing covalent bridges in peptides. However, due to the sensitivity of the peptide backbone and side chains, this method necessitates careful protection/deprotection strategies.

The general guiding principles determining the design of useful cyclic peptides are well-known in the art and are dictated by the need to maintain the antibody reactivity and immunogenicity of the V2 peptide, particularly for induction of broadly reactive, neutralizing antibodies while enhancing its stability as well as the ability to be inserted into a desired scaffold protein without disrupting the "function" of the latter, i.e., immunogenicity and other binding characteristics of the scaffold such as the binding of recombinant V2-CTB to the glycolipid targets of CTB. In addition to testing a cyclic peptide serologically, it may be analyzed more extensively by structural (biophysical) techniques, such as NMR spectroscopy or X-ray crystallographic methods, in solution or when bound to a characterizing broadly-reactive neutralizing monoclonal antibody such as 447-52D (see publication WO04/069863, which is hereby incorporated by reference in its entirety)

The one or more peptides in the present invention can be synthesized by solid phase or solution phase peptide synthesis, recombinant expression, or can be obtained from natural sources. Automatic peptide synthesizers are commercially available from numerous suppliers, such as Applied Biosystems, Foster City, Calif. Standard techniques of chemical peptide synthesis are well known in the art (see e.g., SYNTHETIC PEPTIDES: A USERS GUIDE 93-210 (Gregory A. Grant ed., 1992), which is hereby incorporated by reference in its entirety). Peptide production via recombinant expression can be carried out using bacteria, such as *E. coli*, yeast, insect cells or mammalian cells and expression systems. Procedures for recombinant protein/peptide expression are well known in the art and are described by Sambrook et al., *Molecular Cloning: A Laboratory Manual* (C.S.H.P. Press, NY 2d ed., 1989), which is hereby incorporated by reference in its entirety.

Recombinantly expressed peptides can be purified using any one of several methods readily known in the art, including ion exchange chromatography, hydrophobic interaction chromatography, affinity chromatography, gel filtration, and reverse phase chromatography. The peptide is preferably produced in purified form (preferably at least about 80% to 85% pure, more preferably at least about 90% or 95% pure) by conventional techniques. Depending on whether the recombinant host cell is made to secrete the peptide into growth medium (see U.S. Pat. No. 6,596,509 to Bauer et al., which is hereby incorporated by reference in its entirety), the peptide can be isolated and purified by centrifugation (to separate cellular components from supernatant containing the secreted peptide) followed by sequential ammonium sulfate precipitation of the supernatant. The fraction containing the peptide is subjected to gel filtration in an appropriately sized dextran or polyacrylamide column to separate the peptides from other proteins. If necessary, the peptide fraction may be further purified by HPLC.

Another aspect of the present invention is directed to an immunogenic vaccine composition comprising the linear or cyclized isolated immunogenic peptides or polypeptides described above, and an immunologically and pharmaceutically acceptable vehicle or excipient.

Suitable vehicles and excipients are described in REMINGTON'S PHARMACEUTICAL SCIENCE (19th ed., 1995), which is hereby incorporated by reference in its entirety. The incorporation of such immunologically and pharmaceutically acceptable components depends on the intended mode of administration and therapeutic application of the pharmaceutical composition. Typically, however, the vaccine composition will include a pharmaceutically-acceptable, non-toxic carrier or diluent, which are defined as vehicles commonly used to formulate pharmaceutical compositions for animal or human administration. The diluent is selected so as not to affect the biological activity of the composition. Exemplary carriers or diluents include distilled water, physiological phosphate-buffered saline, Ringer's solutions, dextrose solution, and Hank's solution.

Vaccine compositions can also include large, slowly metabolized macromolecules such as proteins, polysaccharides such as chitosan, polylactic acids, polyglycolic acids and copolymers (such as latex functionalized sepharose, agarose, cellulose), polymeric amino acids, amino acid copolymers, and lipid aggregates (such as oil droplets or liposomes).

The vaccine composition of the present invention may also be supplemented with an immunostimulatory cytokine. Preferred cytokines are GM-CSF (granulocyte-macrophage colony stimulating factor), interleukin 1, interleukin 2, interleukin 12, interleukin 18, or interferon-gamma.

The vaccine composition of the present invention can further contain an adjuvant. One class of preferred adjuvants is aluminum salts, such as aluminum hydroxide, aluminum phosphate, or aluminum sulfate. Such adjuvants can be used with or without other specific immunostimulating agents such as MPL or 3-DMP, QS-21, flagellin, polymeric or monomeric amino acids such as polyglutamic acid or polylysine, or pluronic polyols. Oil-in-water emulsion formulations are also suitable adjuvants that can be used with or without other specific immunostimulating agents such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) Theramide®, or other bacterial cell wall components). A suitable oil-in-water emulsion is MF59® (containing 5% Squalene, 0.5% Tween® 80, and 0.5% Span® 85 (optionally containing various amounts of MTP-PE) formulated into submicron particles using a microfluidizer such as Model 110Y Microfluidizer® (Microfluidics, Newton Mass.) as described in WO90/14837 to Van Nest et al., which is hereby incorporated by reference in its entirety. Other suitable oil-in-water emulsions include SAF (containing 10% Squalene, 0.4% Tween® 80, 5% Pluronic®-blocked polymer L121, and thr-MDP, either microfluidized into a submicron emulsion or vortexed to generate a larger particle size emulsion) and Ribi adjuvant system (RAS; containing 2% squalene, 0.2% Tween® 80, and one or more bacterial cell wall components). Another class of suitable adjuvants are saponin adjuvants, such as Stimulon® (QS-21) or particles generated therefrom such as ISCOMs (immunostimulating complexes) and ISCOMATRIX™. Other suitable adjuvants include incomplete or complete Freund's Adjuvant (IFA). Such adjuvants are generally available from commercial sources.

Another aspect of the present invention relates to a method of inducing a broadly neutralizing antibody response against a V2 epitope of HIV-1 gp120 in a subject. This method comprises administering to the subject the immunogenic peptide, cyclized peptide, or polypeptides, described above, under conditions effective to induce, in the subject, a neutralizing antibody response against the V2 epitope of the HIV-1 gp120. In a preferred embodiment of this aspect, the selected subject is HIV-1 positive.

In accordance with this aspect of the present invention, a neutralizing antibody response is an antibody or response that results in binding and neutralization of at least one group of heterologous HIV-1 viruses that are members of a different subtype or clade than that of the source of the immunizing antigen. Such a response is an active response induced by administration of the immunogenic peptide or polypeptide and represents a means for vaccination against HIV-1.

An MT-2 assay can be performed to measure neutralizing antibody responses. Antibody-mediated neutralization of selected strains or isolates of HIV-1 can be measured in an MT-2 cell-killing assay (Montefiori et al., "Evaluation of Antiviral Drugs and Neutralizing Antibodies to Human Immunodeficiency Virus By a Rapid and Sensitive Microtiter Infection Assay," *J Clin Microbiol.* 26(2):2310-235 (1988), which is hereby incorporated by reference in its entirety). HIV-1.sub.IIIB and HIV-1.sub.MN induce the formation of syncytia in MT-2 cells. The inhibition of the formation of syncytia by the sera shows the activity of neutralizing antibodies present within the sera, induced by vaccination. Immunized test and control sera can be exposed to virus-infected cells (e.g. cells of the MT-2 cell line). Neutralization can be measured by any method that determines viable cells, such as staining, e.g., with Finter's neutral red. Percentage protection can be determined by calculating the difference in absorption between test wells (cells+virus) and dividing this result by the difference in absorption between cell control wells (cells only) and virus control wells (virus only). Neutralizing titers may be expressed, for example, as the reciprocal of the plasma dilution required to protect at least 50% of cells from virus-induced killing.

Another aspect of the present invention relates to a method of inducing a protective and non-neutralizing antibody response against a V2 epitope of HIV-1 gp120 in a subject. This method comprises administering to the subject the immunogenic peptide, cyclized peptide, or polypeptides, as described above, under conditions effective to induce, in the subject, a protective, non-neutralizing antibody response against the V2 epitope of the HIV-1 gp120. In a preferred embodiment of this aspect, the selected subject is HIV-1 positive.

In accordance with this aspect of the present invention, non-neutralizing antibodies will not impair virus entry into cells. However, a non-neutralizing antibody response will trigger antibody-dependent cell-mediated viral inhibition (ADCVI), which may be effective against HIV-1 (Asmal et al., "Antibody Dependent Cell Mediated Viral Inhibition Emerges After Simian Immunodeficiency Virus SIVmac251 Infection of Rhesus Monkeys Coincident With gp140-Binding Antibodies and is Effective Against Neutralization Resistant Viruses," *J. Virol.* 85(11) 5465-5475 (2011), which is hereby incorporated by reference in its entirety).

ADCVI can be measured by infecting polybrene-treated CEM.NKR-CCR5 cells (National Institutes of Health AIDS Research and Reference Program) with a clinical strain of HIV-1 (HIV-$1_{92US657}$). The addition of effector cells from healthy donors and sera from vaccine subjects to the infected target cells can lead to ADCVI. Levels of p24, as determined by ELISA can determine the presence of ADCVI (Forthal et al., "Recombinant gp120 Vaccine-Induced Antibodies Inhibit Clinical Strains of HIV-1 in the Presence of Fc Receptor Bearing Effector Cells and Correlate Inversely with HIV Infection Rate," *J of Immunol.* 178(10): 6596-6603 (2007), which is hereby incorporated by reference in its entirety).

Another aspect of the present invention relates to a method of inducing protective antibodies against a V2 epitope of HIV-1 gp120 in a subject. This method comprises administering to the subject the immunogenic peptide, cyclized peptide, or polypeptide, as described above, under conditions effective to induce, in the subject, a protective antibody response against the V2 epitope of the HIV-1 gp120. In one embodiment, the selected subject is HIV-1 positive.

The presence of a protective humoral immunological response can be determined and monitored by testing a biological sample (e.g., blood, plasma, serum, urine, saliva, feces, CSF or lymph fluid) from the subject for the presence of antibodies directed to the immunogenic component of the administered pharmaceutical composition.

The immunization protocol preferably includes at least one priming dose, followed by one or multiple boosting doses administered over time. An exemplary range for an immunogenically effective amount of the present immunogenic polypeptides is about 5 to about 500 μg/kg body weight. A preferred range is about 10-100 μg/kg.

Compositions of the present invention can be administered by parenteral, topical, intravenous, oral, subcutaneous, intraperitoneal, intranasal, or intramuscular means. The most typical route of administration for compositions formulated to induce an immune response is subcutaneous, although others can be equally effective. The next most common is intramuscular injection. This type of injection is most typically performed in the arm or leg muscles. Intravenous injections as well as intraperitoneal injections, intraarterial, intracranial, or intradermal injections are also effective in generating an immune response.

The compositions of the present invention may be formulated for parenteral administration. Solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

Vaccine formulations suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

When it is desirable to deliver the vaccine of the present invention systemically, it may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing, and/or dispersing agents.

Intraperitoneal or intrathecal administration of the agents of the present invention can also be achieved using infusion pump devices such as those described by Medtronic, Northridge, Calif. Such devices allow continuous infusion of desired compounds avoiding multiple injections and multiple manipulations.

In addition to the formulations described previously, the agents may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The present invention is further directed to an isolated antibody raised against the immunogenic peptide or polypeptide of the present invention. The isolated antibody of the present invention encompasses any immunoglobulin molecule that specifically binds the V2 epitope of HIV-1 gp120. As used herein, the term "antibody" is meant to include intact immunoglobulins derived from natural sources or from recombinant sources, as well as immunoreactive portions (i.e., antigen binding portions) of intact immunoglobulins. The antibodies of the present invention may exist in a variety of forms including, for example, polyclonal antibodies, monoclonal antibodies, intracellular antibodies ("intrabodies"), antibody fragments (e.g. Fv, Fab and F(ab)2), as well as single chain antibodies (scFv), chimeric antibodies and humanized antibodies (Ed Harlow and David Lane, Using Antibodies: A Laboratory Manual (Cold Spring Harbor Laboratory Press, 1999); Houston et al., "Protein Engineering of Antibody Binding Sites Recovery of Specific Activity in an Anti-Digoxin Single-Chain Fv Analogue Produced in *Escherichia coli," Proc Natl Acad Sci USA* 85:5879-5883 (1988); Bird et al, "Single-Chain Antigen-Binding Proteins," *Science* 242:423-426 (1988), each of which is hereby incorporated by reference in its entirety).

Antibodies of the present invention may also be synthetic antibodies. A synthetic antibody is an antibody which is generated using recombinant DNA technology, such as, for example, an antibody expressed by a bacteriophage. Alternatively, the synthetic antibody is generated by the synthesis of a DNA molecule encoding and expressing the antibody of the present invention or the synthesis of an amino acid specifying the antibody, where the DNA or amino acid sequence has been obtained using synthetic DNA or amino acid sequence technology which is available and well known in the art.

Methods for monoclonal antibody production may be carried out using the techniques described herein or other well-known in the art (MONOCLONAL ANTIBODIES—PRODUCTION, ENGINEERING AND CLINICAL APPLICATIONS (Mary A. Ritter and Heather M. Ladyman eds., 1995), which is hereby incorporated by reference in its entirety). Generally, the process involves obtaining immune cells (lymphocytes) from the spleen of a mammal which has been previously immunized with the antigen of interest (i.e., a polymerized first or second peptide or fusion peptide) either in vivo or in vitro.

The antibody-secreting lymphocytes are then fused with myeloma cells or transformed cells, which are capable of replicating indefinitely in cell culture, thereby producing an immortal, immunoglobulin-secreting cell line. Fusion with mammalian myeloma cells or other fusion partners capable of replicating indefinitely in cell culture is achieved by standard and well-known techniques, for example, by using polyethylene glycol (PEG) or other fusing agents (Milstein and Kohler, "Derivation of Specific Antibody-Producing Tissue Culture and Tumor Lines by Cell Fusion," Eur J Immunol 6:511 (1976), which is hereby incorporated by reference in its entirety). The immortal cell line, which is preferably murine, but may also be derived from cells of other mammalian species, is selected to be deficient in enzymes necessary for the utilization of certain nutrients, to be capable of rapid growth, and have good fusion capability. The resulting fused cells, or hybridomas, are cultured, and the resulting colonies screened for the production of the desired monoclonal antibodies. Colonies producing such antibodies are cloned, and grown either in vivo or in vitro to produce large quantities of antibody.

Alternatively monoclonal antibodies can be made using recombinant DNA methods as described in U.S. Pat. No. 4,816,567 to Cabilly et al, which is hereby incorporated by reference in its entirety. The polynucleotides encoding a monoclonal antibody are isolated from mature B-cells or hybridoma cells, for example, by RT-PCR using oligonucleotide primers that specifically amplify the genes encoding the heavy and light chains of the antibody. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries (McCafferty et al., "Phage Antibodies: Filamentous Phage Displaying Antibody Variable Domains," Nature 348: 552-554 (1990); Clackson et al., "Making Antibody Fragments using Phage Display Libraries," Nature 352:624-628 (1991); and Marks et al., "By-Passing Immunization. Human Antibodies from V-Gene Libraries Displayed on Phage," J. Mol. Biol. 222:581-597 (1991), which are hereby incorporated by reference in their entirety).

The polynucleotide(s) encoding a monoclonal antibody can further be modified using recombinant DNA technology to generate alternative antibodies. For example, the constant domains of the light and heavy chains of a mouse monoclonal antibody can be substituted for those regions of a human antibody to generate a chimeric antibody. Alternatively, the constant domains of the light and heavy chains of a mouse monoclonal antibody can be substituted for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity and affinity of a monoclonal antibody.

The monoclonal antibody of the present invention can be a humanized antibody. Humanized antibodies are antibodies that contain minimal sequences from non-human (e.g., murine) antibodies within the variable regions. Such antibodies are used therapeutically to reduce antigenicity and human anti-mouse antibody responses when administered to a human subject. In practice, humanized antibodies are typically human antibodies with minimal to no non-human sequences. A human antibody is an antibody produced by a human or an antibody having an amino acid sequence corresponding to an antibody produced by a human.

Procedures for raising polyclonal antibodies are also well known. Typically, such antibodies can be raised by administering the peptide or polypeptide containing the epitope of interest (i.e. polymerized first or second peptides or fusion peptides) subcutaneously to rabbits (e.g. New Zealand white rabbits), goats, sheep, swine or donkeys which have been bled to obtain pre-immune serum. The antigens can be injected in combination with an adjuvant. The rabbits are bled approximately every two weeks after the first injection and periodically boosted with the same antigen three times every six weeks. Polyclonal antibodies are recovered from the serum by affinity chromatography using the corresponding antigen to capture the antibody. This and other procedures for raising polyclonal antibodies are disclosed in Ed Harlow and David Lane, USING ANTIBODIES: A LABORATORY MANUAL (Cold Spring Harbor Laboratory Press, 1988), which is hereby incorporated by reference in its entirety.

In addition to whole antibodies, the present invention encompasses binding portions of such antibodies. Such binding portions include the monovalent Fab fragments, Fv fragments (e.g., single-chain antibody, scFv), and single variable $V_H$ and $V_L$ domains, and the bivalent F(ab')$_2$ fragments, Bis-scFv, diabodies, triabodies, minibodies, etc. These antibody fragments can be made by conventional procedures, such as proteolytic fragmentation procedures, as described in James Goding, MONOCLONAL ANTIBODIES:PRINCIPLES AND PRACTICE 98-118 (Academic Press, 1983) and Ed Harlow and David Lane, ANTIBODIES: A LABORATORY MANUAL (Cold Spring Harbor Laboratory, 1988), which are hereby incorporated by reference in their entirety, or other methods known in the art.

It may further be desirable, especially in the case of antibody fragments, to modify the antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Antibody mimics are also suitable for use in accordance with the present invention. A number of antibody mimics are known in the art including, without limitation, those known as monobodies, which are derived from the tenth human fibronectin type III domain ($^{10}$Fn3) (Koide et al., "The Fibronectin Type III Domain as a Scaffold for Novel Binding Proteins," *J. Mol Biol* 284:1141-1151 (1998); Koide et al., "Probing Protein Conformational Changes in Living Cells by Using Designer Binding Proteins: Application to the Estrogen Receptor," *Proc Natl Acad Sci USA* 99:1253-1258 (2002), each of which is hereby incorporated by reference in its entirety); and those known as affibodies, which are derived from the stable alpha-helical bacterial receptor domain Z of staphylococcal protein A (Nord et al., "Binding Proteins Selected from Combinatorial Libraries of an alpha-helical Bacterial Receptor Domain," *Nature Biotechnol* 15(8):772-777 (1997), which is hereby incorporated by reference in its entirety).

The present invention is further directed to a method of detecting whether a subject is infected with HIV-1. This method includes providing a sample from the subject. The sample is contacted with the immunogenic peptide described above under conditions effective to cause an immunogenic reaction between antibodies in the sample and the immunogenic peptide. Any subject, where the contacting results in the immunogenic reaction, is identified as being infected with HIV-1. The diagnosis of HIV-1 is based on the detection of V2-specific antibodies in the subject. The presence of antibodies reactive with the V2-specific peptides can be detected using standard electrophoretic and immunodiagnostic techniques, including immunoassays such as competition, direct reaction, or sandwich type assays. Such assays include, but are not limited to: western blots; agglutination tests; enzyme-labeled and mediated immunoassays, such as ELISAs; biotin/avidin type assays; radioimmunoassays; immunoelectrophoresis; immunoprecipitation, etc. The reactions generally involve using labels such as fluorescent, chemiluminescent, radioactive, or enzymatic labels or dye molecules, or other methods for detecting the formation of a complex between the antigen and the antibody.

EXAMPLES

The following examples are provided to illustrate embodiments of the present invention but they are by no means intended to limit its scope.

Materials and Methods for Examples 1-4

Specimens.

The initial pilot studies were performed using various sets of plasma from the RV144 participants which were selected randomly, evenly balanced for men and women, and derived from participants at visit 1 (pre-bleed), visit 8 (week 26 after the first immunization [two weeks after the last immunization]), and visit 9 (52 weeks). The pilot studies were performed with plasma sets C (SZP, PB), A and L (GT, BH), and Z (MR, NK). Subsequently, case-control plasma specimens, described above, were tested for the primary and secondary variables selected as described above and in Haynes et al., "Immune Correlates Analysis of the ALVAC-AIDSVAX HIV-1 Vaccine Efficacy Trial," *N Engl J Med.* 366:1275-1286 (2012), which is hereby incorporated by reference in its entirety.

Written informed consent and counseling was conducted as described previously (Rerks-Ngarm et al., "Vaccination with ALVAC and AIDSVAX to Prevent HIV-1 Infection in Thailand," *N Engl J Med* 361:2209-2220 (2009); Haynes et al., "Immune Correlates Analysis of the ALVAC-AIDSVAX HIV-1 Vaccine Efficacy Trial," *N Engl J Med.* 366:1275-1286 (2012), each of which is hereby incorporated by reference in its entirety), and the protocol was reviewed by the ethics committees of the Thai Ministry of Public Health, the Royal Thai Army, Mahidol University, and the Human Subjects Research Review Board of the U.S. Army Medical Research and Materiel Command. It was also independently reviewed and endorsed by the World Health Organization and the Joint United Nations Program on HIV/AIDS and by the AIDS Vaccine Research Working Group of the National Institute of Allergy and Infectious Diseases at the National Institutes of Health. The manufacturers were full trial collaborators and were a part of the Phase III trial steering committee.

ELISA for Cyclic Peptides and Recombinant gp120 (NK).

This assay was previously described (Haynes et al., "Immune Correlates Analysis of the ALVAC-AIDSVAX HIV-1 Vaccine Efficacy Trial," *N Engl J Med.* 366:1275-1286 (2012), which is hereby incorporated by reference in its entirety). Briefly, U-bottom ELISA plates were coated with either 1 µg/ml of cyclic peptide (Table 1) or with 3 µg/ml of AIDSVAX recombinant gp120 immunogen A244 or MN.

TABLE 1

V2-Related Reagents and Assays Used in the Pilot and Case-Controlled Analysis

| Assay and Reagents/Lab PI | | Used for Pilot Study | Used for Case-control |
|---|---|---|---|
| ELISA/Karasavva | | | |
| [a]Cyclic V2 (AAs 157-198) | CSFNMTTELRDKKQKVHALFYKLDIVPIEDNT (SEQ ID NO: 66) | + | + |
| Cyclic scrambled V2 crown | CSFNMTTELRDKQVLFKDIHKIVKPLYAEDNTSSSEYRLINC (SEQ ID NO: 69) | + | + |
| Cyclic scrambled V2 flanks | CENLTDKMFTSRKQKVHALFYKLDIVPISESRLDETNYNISC (SEQ ID NO: 70) | + | + |
| ELISA/Zolla-Pazner | | | |
| [b]Peptide 1: Most polar V2 sequence (AAs165-185) | LRDKKQRVYSLFYKLDVVQIN (SEQ ID NO: 3) | | + |

TABLE 1-continued

V2-Related Reagents and Assays Used in the Pilot and Case-Controlled Analysis

| Assay and Reagents/Lab PI | | Used for Pilot Study | Case-control |
|---|---|---|---|
| Peptide 2 Most common 40 AA V2 sequence | IRDKVQKEYALFYKLDVVPID (SEQ ID NO: 4) | + | |
| Peptide 3 Most polar 40 AA V2 sequence | LRDKKQQVYSLFYRLDIEKIN (SEQ ID NO: 5) | + | |
| Peptide 4 Consensus 40 AA V2 sequence | IRDKKQKEYALFYKLDVVPID (SEQ ID NO: 6) | + | |
| Peptide 6: First 14 AA of Peptide 1 (AAs 165-178) | *LRDKKQRVYSLFYK* (SEQ ID NO: 7) | + | + |
| Peptide 6G: First 14 AA of Peptide 1 with linker | GGGLRDKKQRVYSLFYK (SEQ ID NO: 10) | + | |
| Peptide 7: Central 14-mer of peptide 1 | *KQRVYSLFYKLDVV* (SEQ ID NO: 8) | + | |
| Peptide 8: C-term 13-mer Peptide 1 | *YSLFYKLDVVQIN* (SEQ ID NO: 9) | + | |
| Peptide 17: L165I Mutant of Peptide 6 | GGGIRDKKQRVYSLFYK (SEQ ID NO: 11) | + | |
| Peptide 18: K169V Mutant of Peptide 6 | GGGLRDKVQRVYSLFYK (SEQ ID NO: 12) | + | |
| Peptide 19: V172E Mutant of Peptide 6 | GGGLRDKKQREYSLFYK (SEQ ID NO: 13) | + | |
| Peptide 20: S174A Mutant of Peptide 6 | GGGLRDKKQRVYALFYK (SEQ ID NO: 14) | + | |
| [a]Cyclic V2 (AAs 157-198) | *CSFNMTTELRDKKQKVHAL*FYKLDIVPIEDNTSSSEYRLINC (SEQ ID NO: 66) | + | + |
| gp70-V1V2 [from subtype B Case A2] | CVTLNCIDLRNATNATSNSNTTNTTSSSGGLMMEQGEIKNCSFNITTSIRDKVQ KEYALFYKLDIVPIDNPANSTNYRLISC (SEQ ID NO: 71) | + | + |
| ELISA/Berman | | | |
| V2 A244-92TH023 peptide | NMTTELRDKKQKVHALFYK (SEQ ID NO: 72) | + | + |
| V2 MN peptide | ITTSIGDKMQKEYALLYKLDIEP (SEQ ID NO: 73) | + | + |
| ELISA/Tomaras | | | |
| V2 peptide K178 | KK*KVHALFYKLDIVPIED*KKK (SEQ ID NO: 74) | + | |
| SPR/Rao | | | |
| Cyclic V2 scrambled crown | *CSFNMTTELRDK*QVLFKDIHKIVKPLYA*EDNTSSSEYRLINC* (SEQ ID NO: 69) | + | + |
| [a]Cyclic V2 (AAs 157-198) | *CSFNMTTELRDKKQK*VHALFYKLDIVPIED*NTSSSEYRLINC* (SEQ ID NO: 66) | + | + |

TABLE 1-continued

V2-Related Reagents and Assays Used in the Pilot and Case-Controlled Analysis

| Assay and Reagents/Lab PI | | Used for | |
|---|---|---|---|
| | | Pilot Study | Case-control |
| Luminex/Tomaras | | | |
| IgG binding to biotinylated V2 peptide K178 | KK*KVHALFYKLDIVPIED*KKK (SEQ ID NO: 74) | + | + |
| IgA binding to biotinylated V2 peptide K178 | KK*KVHALFYKLDIVPIED*KKK (SEQ ID NO: 74) | + | + |
| *Hotspot/ Montefiori | * | + | + |

<sup>a</sup>"Cyclic V2 (amino acids 157-198)" was used in assays in three labs as shown. Throughout this table, bold italicized V2 sequences are identical to the subtype E 92TH023 used in the prime; underlined sequences represent scrambled sequences or linkers; italicized sequences represent the sequence the central amino acidss in an extremely polar V2 in subtype A strain QB585.2102M.Ev1v5.C with individual mutations shown in bold; plain black represents sequences chosen for particular properties, as described; bold underlined sequences represent the V1V2 from subtype B Case A2 (Pinter et al., "Potent Neutralization of Primary HIV-1 Isolates By Antibodies Directed Against Epitopes Present in the V1/V2 Domain of HIV-1 gp120," Vaccine 16: 1803-1811 (1998), which is hereby incorporated by reference in its entirety) and the central 23-mer of V2 from subtype B strain MN.
<sup>b</sup>All peptides were biotinylated at the N-terminus with the exception of peptide K178 and peptide V2 A244-92TH023 which were biotinylated at the C-terminus.
*Multiple V2 peptides from various strains (see Table 1 and Karasavvas et al., "The Thai Phase Iii Clinical Trial (RV144) Induces the Generation of Antibodies that Target a Conserved Region Within the V2 Loop of gp120; The Thai Phase Iii Clinical Trial (RV144) Induces the Generation of Antibodies that Target a Conserved Region Within the V2 Loop of gp120", Abstract OA07.08 LB; Bangkok, Thailand. pp. OA07.08 LB (2011), which is hereby incorporated by reference in its entirety).

After washing, two-fold serial dilutions of plasma at an initial dilution of 1:100 or, alternatively, anti-V2 human monoclonal antibodies 2158 or 697-D (Gorny et al., "Human Anti-V2 Monoclonal Antibody That Neutralizes Primary But Not Laboratory Isolates of HIV-1," *J. Virol.* 68:8312-8320 (1994); Pinter at al., "The V1/V2 Domain of gp120 is a Global Regulator of Sensitivity of Primary Human Immunodeficiency Virus Type 1 Isolates to Neutralization by Antibodies Commonly Induced Upon Infection," *J. Virol.* 78:5205-5215 (2004), each of which is hereby incorporated by reference in its entirety) were used at concentrations of 0.002-10 µg/ml. Color was developed with HRP-conjugated goat anti-human IgG and substrate, and read A405 nm. The background value was determined from wells that did not contain recombinant proteins or peptides.

Biotinylated Linear Peptide ELISAs (SZP).

This assay was previously described (Haynes et al., "Immune Correlates Analysis of the ALVAC-AIDSVAX HIV-1 Vaccine Efficacy Trial," *N Engl J Med.* 366:1275-1286 (2012), which is hereby incorporated by reference in its entirety). Briefly, StreptaWell ELISA plates (Roche) were coated with 1 µg/ml of one of several N-terminus biotinylated linear V2 peptides (Table 1); the plates were washed and incubated with RV144 plasma specimens diluted 1:100 in RPMI medium containing 15% fetal bovine sera. Alkaline phosphatase (AP)-conjugated goat anti-human IgG and diethanolamine substrate were used to develop color which was read at A405 nm. At each step, every well contained 50 µl; specimens were run in duplicate in each experiment, and three experiments were performed.

Binding ELISA with gp70-V1V2 (SZP).

This method was previously described (Haynes et al., "Immune Correlates Analysis of the ALVAC-AIDSVAX HIV-1 Vaccine Efficacy Trial," *N Engl J Med.* 366:1275-1286 (2012), which is hereby incorporated by reference in its entirety). Briefly, plates were coated with 1 µg/ml gp70-V1V2 (Table 1 and Pinter et al., "Potent Neutralization of Primary HIV-1 Isolates by Antibodies Directed Against Epitopes Present in the V1N2 Domain of HIV-1 gp120," *Vaccine* 16:1803-1811 (1998), which is hereby incorporated by reference in its entirety), washed, and then incubated for 1.5 h at 37° C. with RV144 plasma diluted 1:100 in RPMI containing 15% fetal bovine sera. After further washing, bound antibodies were visualized using AP-conjugated goat anti-human IgG and diethanolamine substrate, and read at 405 nm. At each step, every well contained 50 µl; specimens were run in duplicate in each experiment, and three experiments were performed.

V2 Linear Peptide ELISA (PB).

These assays were performed as previously described (Gilbert et al., "Correlation Between Immunologic Responses to a Recombinant Glycoprotein 120 Vaccine and Incidence of HIV-1 Infection in a Phase 3 HIV-1 Preventative Vaccine Trial," *J Infect Dis.* 191:666-677 (2005), which is hereby incorporated by reference in its entirety). Briefly, plates were coated with 0.5 µg/well of peptide (Table 1) and incubated overnight at 4° C. Three-fold dilutions of test sera were run in duplicate using a starting dilution of 1:30. HRP-labeled anti-human IgG and substrate (OPD) were used to develop color.

ELISAs of Linear and Cyclic Peptides and gp70-V1V2 (GT).

Direct binding ELISAs were conducted as previously described (Haynes et al., "Immune Correlates Analysis of the ALVAC-AIDSVAX HIV-1 Vaccine Efficacy Trial," *N Engl J Med.* 366:1275-1286 (2012), which is hereby incorporated by reference in its entirety) in 384-well ELISA plates coated with 2 µg/ml of linear or cyclic V2 peptides or gp70-V1V2 and incubated with three-fold serial dilutions of plasma at a starting dilution of 1:50, followed by washing and incubation with 10 µl of HRP-conjugated goat anti-human Ig secondary antibody and substrate (SureBlue Reserve™) Plates were read at 450 nm.

Overlapping Peptide Microarray Assay (DM).

The arrays measured reactivity with 15-mer peptides with 12 residue overlaps. Raw peptide microarray data were processed and analyzed as described in Tomaras et al. "Initial B-cell Responses to Transmitted Human Immunodeficiency Virus Type 1: Virion-Binding Immunoglobulin M (IgM) and IgG Antibodies Followed by Plasma Anti-gp41 Antibodies With Ineffective Control of Initial Viremia," *J. Virol.* 82:12449-12463 (2008), which is hereby incorporated by reference in its entirety. Peptide sequences were provided by LANL to cover the entire gp160 HIV Env from six HIV-1 Group M subtypes (A, B, C, D, CRF01_AE and CRF02_AG) for a total of 1423 peptides. The specific peptides were determined by LANL's method for generating the mosaic peptide set (Ngo et al., "Identification and Testing of Control Peptides for Antigen Microarrays," *Journal of Immunological Methods.* 343:68-78 (2009), which is hereby incorporated by reference in its entirety) and were manufactured by JPT Peptide Technologies (Berlin, Germany).

Surface Plasmon Resonance (MR).

Measurements were conducted with a Biacore® T100 as previously described (Haynes et al., "Immune Correlates Analysis of the ALVAC-AIDSVAX HIV-1 Vaccine Efficacy Trial," *N Engl J Med.* 366:1275-1286 (2012), which is hereby incorporated by reference in its entirety). Briefly, lysozyme (reference surface) and streptavidin (for peptide capture) were immobilized onto CM5 chips. Biotinylated V2 peptides (1 µM) (Table 1) were manually injected over the streptavidin-coated chip surface. Heat-inactivated plasma samples diluted 1:50 were injected over the chip surface followed by a dissociation period, after which a 50 nM solution of affinity-purified γ-chain-specific sheep anti-human IgG was passed over the peptide coated-Ig bound surface. Non-specific binding was subtracted and data analysis was performed using BIAevaluation™ 4.1 software. Case-control samples were run in triplicate.

IgG and IgA Binding Multiplex Assays (GT). These assays were performed as previously described (Haynes et al., "Immune Correlates Analysis of the ALVAC-AIDSVAX HIV-1 Vaccine Efficacy Trial," *N Engl J Med.* 366:1275-1286 (2012); Tomaras et al., "Initial B-cell Responses to Transmitted Human Immunodeficiency Virus Type 1: Virion-Binding Immunoglobulin M (IgM) and IgG Antibodies Followed by Plasma Anti-gp41 Antibodies With Ineffective Control of Initial Viremia," *J. Virol.* 82:12449-12463 (2008), each of which is hereby incorporated by reference in its entirety) using peptide K178 which represents a linear portion of V2 from immunogens A244 and 92TH023 (Table 1). HIV-specific antibody isotypes were detected with goat anti-human IgA and mouse anti-human IgG.

Statistical Analyses.

Immune biomarkers measured two weeks after the last immunizing dose were assessed as correlates of subsequent infection risk using the previously described statistical analysis plan (Haynes et al., "Immune Correlates Analysis of the ALVAC-AIDSVAX HIV-1 Vaccine Efficacy Trial," *N Engl J Med.* 366:1275-1286 (2012), which is hereby incorporated by reference in its entirety). Briefly, for each immune biomarker, logistic regression accounting for the sampling design was used to estimate the odds ratio (OR) of infection, controlling for gender and baseline behavioral risk. The OR was estimated both for the immune biomarker as a categorical variable and for variables with greater than 50% of vaccines exhibiting a positive response, as a quantitative variable (scaled to have a SD=1). For the categorical analysis, if the positive response rate is less than 50%, then the OR compares positive vs. negative responders. If the positive response rate is 50-85%, then the OR compares high vs. negative where high is above the median of the positive responders. For positive response rates >85%, the OR compares high vs. low where high and low are the upper and bottom tertiles of the response for vaccine recipients. The statistical analysis plan was finalized before data analysis and is described in detail in Haynes et al., "Immune Correlates Analysis of the ALVAC-AIDSVAX HIV-1 Vaccine Efficacy Trial," *N Engl J Med.* 366:1275-1286 (2012), which is hereby incorporated by reference in its entirety.

The lasso model selection procedure (Friedman et al., "Regularization Paths for Generalized Linear Models Via Coordinate Descent," *J Stat Softw.* 33:1-22 (2010), which is hereby incorporated by reference in its entirety) as implemented in the R software package was used to assess the ability of 12 V2 variables from Table 2 to predict infection when included in a multivariate logistic model adjusting for gender and behavioral risk score.

TABLE 2

Response Rate and Odds Ratios (ORs) Calculated From the Case Control Specimens Tested With 13 V2 Variables.

| Assay | Investigator | Institution | Quantitative OR[1,2] | P value | Categorical OR[1,3] | P value |
|---|---|---|---|---|---|---|
| V2 cyclic peptides - ELISA | Nicos Karasavvas | AFRIMS | | | | |
| Cyclic V2 (AAs 157-198) | | | NA | NA | 0.82 | 0.63 |
| Cyclic V2 scrambled crown | | | NA | NA | NA | NA |
| Cyclic V2 scrambled flanks | | | 0.76 | 0.10 | 0.84 | 0.66 |
| V2 cyclic peptides - SPR | Mangala Rao | USMHRP | | | | |
| Cyclic V2 scrambled crown | | | 0.79 | 0.18 | 0.90 | 0.80 |
| Cyclic V2 (AAs 157-198) | | | 0.81 | 0.24 | 0.84 | 0.66 |
| V2 reagents - ELISA | Susan Zolla-Pazner | New York University | | | | |
| Cyclic V2 (AAs 157-198) | | | 0.82 | 0.26 | 0.65 | 0.31 |
| Biotin V2 Peptide 6 (AAs 165-178) | | | 0.95 | 0.80 | 0.85 | 0.76 |
| gp70-V1V2 | | | 0.70 | 0.06 | 0.43 | 0.06 |
| V2 linear peptides - ELISA | Philip Berman | University of California, Santa Cruz | | | | |
| V2 MN peptide | | | NA | NA | 0.41 | 0.25 |
| V2 A244-92TH023 peptide | | | 0.90 | 0.57 | 0.88 | 0.74 |
| IgA and IgG Abs vs. V2 peptide - Luminex | Georgia Tomaras | Duke University | | | | |
| IgA V2 A244 K178 peptide | | | NA | NA | 0.79 | 0.77 |
| IgG V2 A244 K178 peptide | | | NA | NA | 1.02 | 0.95 |

TABLE 2-continued

Response Rate and Odds Ratios (ORs) Calculated From the
Case Control Specimens Tested With 13 V2 Variables.

| Assay | Investigator | Institution | Quantitative | | Categorical | |
|---|---|---|---|---|---|---|
| | | | OR[1,2] | P value | OR[1,3] | P value |
| Peptide Microarray V2 Hotspot analysis | David Montefiori | Duke University | 0.64 | 0.03 | 0.32 | 0.02 |

[1]Estimated odds ratios are computed using a logistic regression model accounting for the sampling design and adjusting for gender and behavioral risk score, as described in Haynes et al., "Immune Correlates Analysis of the ALVAC-AIDSVAX HIV-1 Vaccine Efficacy Trial," *N Engl J Med.* 366:1275-1286 (2012), which is hereby incorporated by reference in its entirety.
[2]Estimated odds ratio per one standard deviation increment in the immune biomarker; not available (NA) if response rates, when applicable, are less than 50%. For example, the OR of 0.70 (ELISA binding to gp70-V1V2) means that for every higher SD value, the rate of infection is 10 reduced by 30%, while the OR of 0.43 means that vaccinees with responses in the upper third had an infection rate 57% lower than vaccinees with responses in the lower third.
[3]Estimated odds ratios comparing subgroups defined by high vs. low responses except for two (IgA V2 A244 K178 and V2 MN) which compare positive vs. negative response and one (biotin V2 peptide 6) which compares high vs. negative; not available (NA) for Cyclic V2 scrambled crown (ELISA) which has no positive responses.

The cyclic V2 scrambled crown variable was excluded, because it had no positive responses. Two of the variables with low response rates, IgA V2 A244 K178 peptide and V2 MN peptide, were dichotomized as 1 for response and 0 for non-response, while the remaining ten variables were included on a quantitative scale. The best parsimonious model was chosen based on the average area under the receiver operating characteristic curve derived from 1,000 10-fold cross-validation splits.

Example 1

Antigenicity of the Boosting Immunogens Used

In RV144, the V2 sequence in the recombinant ALVAC priming immunogen derived from subtype E strain 92TH023 was:

(SEQ ID NO: 66)
[157]CSFNMTTELRDKKQKVHALFYKLDIVPIEDNTSS.SEYRLINC[198].

The V2 sequence in the protein boosting gp120 immunogen AIDSVAX E (strain A244) was (SEQ ID NO: 67)
[157]CSFNMTTELRDKKQKVHALFYKLDIVPIEDNNDS.SEYRLINC[198]

The V2 sequence of the protein boosting gp120 immunogen AIDVAX B (strain MN) was:

(SEQ ID NO: 68)
[157]CSFNITTSIGDKMQKEYALLYKLDIEPI.DN.DSTS.YRLISC[198]

Insertion of periods in the sequences allows for alignment. Numbering shown and used throughout this report is that assigned to strain HxB2 (Ratner et al., "Complete Nucleotide Sequences of Functional Clones of the AIDS Virus," *AIDS Res Hum Retroviruses* 3:57-69 (1987), which is hereby incorporated by reference in its entirety).

The antigenic reactivity of the V2 region in AIDSVAX B and E was assessed using human anti-V2 monoclonal antibodies 697D and 2158 (Gorny et al., "Human Anti-V2 Monoclonal Antibody That Neutralizes Primary But Not Laboratory Isolates of HIV-1," *J. Virol.* 68:8312-8320 (1994); Pinter at al., "The V1/V2 Domain of gp120 is a Global Regulator of Sensitivity of Primary Human Immunodeficiency Virus Type 1 Isolates to Neutralization by Antibodies Commonly Induced Upon Infection," *J Virol.* 78:5205-5215 (2004), each of which is hereby incorporated by reference in its entirety). As shown in FIG. 1, the titration curves for each of these monoclonal antibodies with the two boosting immunogens could be superimposed, with half-maximal binding achieved at 0.0057 and 0.0055 μg/ml of monoclonal antibody 697D, and 0.0041 and 0.0039 μg/ml of monoclonal antibody 2158 vs. AIDSVAX A244 and AIDSVAX MN, respectively. This analysis suggests that, with respect to the highly conformational V2 epitopes recognized by these monoclonal antibodies (Gorny et al., "Functional and Immunochemical Cross-Reactivity of V2-specific Monoclonal Antibodies from Human Immunodeficiency Virus Type 1-infected Individuals," *Virology* 427: 198-207 (2012); Pinter et al., "The V1/V2 Domain of gp120 is a Global Regulator of Sensitivity of Primary Human Immunodeficiency Virus Type 1 Isolates to Neutralization by Antibodies Commonly Induced Upon Infection," *J Viro.l* 78: 5205-5215 (2004); Gorny, "Production of Human Monoclonal Antibodies Via Fusion of Epstein-Barr Virus-Transformed Lymphocytes with Heteromyeloma," In: Celis, editor. *In: Cell Biology: A Laboratory Handbook: Academic Press* 276-281 (1994), each of which is hereby incorporated by reference in its entirety), the antigenicity of the A244 and MN gp120 immunogens are similar. Notably, these two monoclonal antibodies also bind to gp70-V1V2 (Gorny et al., "Functional and Immunochemical Cross-Reactivity of V2-specific Monoclonal Antibodies from Human Immunodeficiency Virus Type 1-infected Individuals," *Virology* 427: 198-207 (2012); Karasavvas et al., "The Thai Phase Iii Clinical Trial (RV144) Induces the Generation of Antibodies that Target a Conserved Region Within the V2 Loop of gp120; The Thai Phase Iii Clinical Trial (RV144) Induces the Generation of Antibodies that Target a Conserved Region Within the V2 Loop of gp120," *Abstract OA*07.08 LB; Bangkok, Thailand. pp. OA07.08 LB (2011), each of which is hereby incorporated by reference in its entirety).

Example 2

Figure 2:
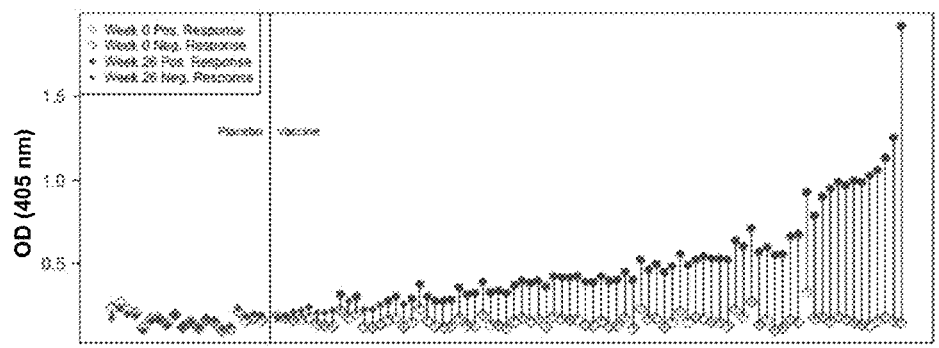
FIG. 2 shows ELISA reactivity with gp70-V1V2 of plasma specimens used in the pilot studies of the RV144 clinical vaccine trial (Set C). The results from one of three experiments are shown. The open and filled blue diamonds depict negative responses at weeks 0 and 26, respectively. The open and closed red circles depict positive responses at weeks 0 and 26, respectively. Each vertical line connects a single patient's specimen drawn at Week 0 and Week 26. The specimens are ordered by the difference in reactivity between the Week 0 and Week 26 specimens, with the biggest increasers on the right. Plasma were tested at a final dilution of 1:100, and a positive response was defined as being >0.276, the cut-off OD value which was defined as the mean+3 standard deviations based on values derived from vaccines at week 0 (the pre-immunization time point).
Figure 3:
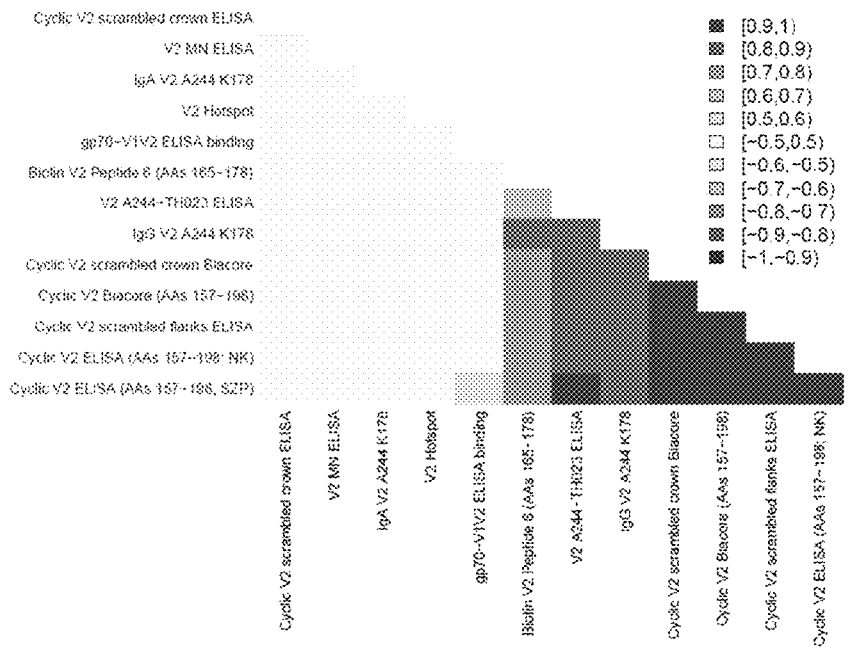
FIG. 3 shows Spearman rank correlations between the V2 assays run in the case-control study.

The V2 Antibody Response in RV144 can be Detected with Both Linear and V1V2-Scaffolded Antigens A gp70-V1V2 scaffolded protein carrying the V1 and V2 loops from a clade B strain, case A2, was previously described (Pinter et al., "Potent Neutralization of Primary HIV-1 Isolates by Antibodies Directed Against Epitopes Ppresent in the V1/V2 Domain of HIV-1 gp120," *Vaccine* 16:1803-1811 (1998), which is hereby incorporated by reference in its entirety). When Set C plasma specimens (from 20 placebo and 80 vaccine recipients) were tested in the pilot studies at a dilution of 1:100, none of the specimens from the placebo recipients contained detectable antibodies to gp70-V1V2. In contrast, the plasma of 67 of 80 (84%) vaccine recipients contained antibodies reactive with this reagent (FIG. 2). Moreover, the dynamic range of the assay was large, covering an optical density range from the cut-off, 0.276 OD units, to 1.918. A relatively poor correlation was found between this assay and other assays that measured various V2 variables, suggesting that the antibody response measured with gp70-V1V2 represents a unique "immunologic space" (FIG. 3).

The frequency of V2 responses detected with pilot study specimens derived from vaccines varied with the assay used, ranging from 6% for IgA antibodies reactive with a linear V2 peptide (K178) when measured by Luminex (see Table 1 and Haynes et al., "Immune Correlates Analysis of the ALVAC-AIDSVAX HIV-1 Vaccine Efficacy Trial," *N Engl Med.* 366:1275-1286 (2012), which is hereby incorporated by reference in its entirety) to 97% for IgG antibodies reactive with an A244 (subtype E) cyclic V2 peptide (see Table 1 and Karasavvas et al., "The That Phase Iii Clinical Trial (RV144) Induces the Generation of Antibodies that Target a Conserved Region Within the V2 Loop of gp120; The Thai Phase Iii Clinical Trial (RV144) Induces the Generation of Antibodies that Target a Conserved Region Within the V2 Loop of gp120", *Abstract OA07.08 LB*; Bangkok, Thailand. pp. OA07.08 LB (2011), which is hereby incorporated by reference in its entirety).

Figure 4:
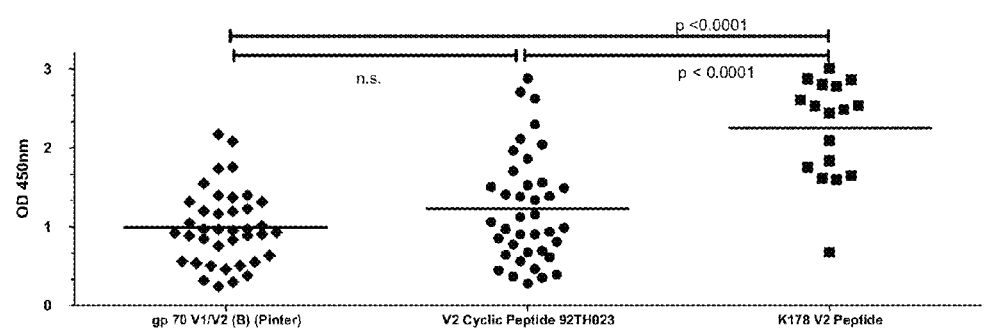
FIG. 4 shows ELISA reactivity of anti-V2 IgG antibodies in plasma from vaccine recipients in the RV144 pilot study (Set L) against three different V2 antigens (gp70-V1V2, V2 cyclic peptide from clade E strain 92TH023, and the K178 V2 peptide) run in parallel in the same assay at a plasma dilution of 1:50. Data shown are from one of two experiments. Plasma from placebo recipients were negative. Statistical comparisons between groups for positive responders were performed using Student's t-test.

When reactivity to various V2 reagents were compared in parallel by ELISA, the response to the K178 peptide was significantly stronger than that to gp70-V1V2 or to cyclic V2 peptide (amino acids 157-198), as shown in FIG. 4. Thus, the RV144 vaccine induced antibodies that reacted to both scaffolded-V1V2 and to linear V2 peptides, but the response to the latter appears to be stronger.

Example 3

Figure 5:
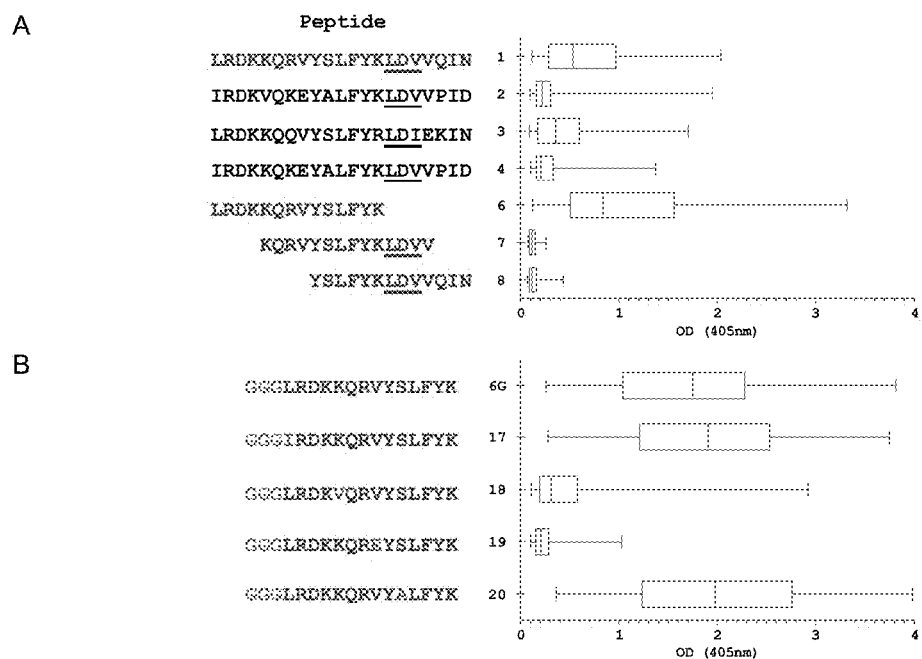
FIGS. 5A-B show boxplots showing ELISA reactivity of V2 peptides with plasma (diluted 1:100) from 80 vaccines' specimens from the pilot study (Set C). The distributions of the reactivities are shown where the left edge of each box equals the 25th percentile; the vertical line in each box is the 50th percentile, and the right edge of each box equals the 75th percentile. The boxplots were prepared using the scientific graphing program, GraphPad Prism, with "whiskers" showing the minimum and maximum responses.

Delineation of the Linear V2 Epitopes Recognized by Plasma Antibodies from Vaccines For fine mapping of linear V2 epitopes recognized by antibodies in the plasma of RV144 vaccines, four 21-mer peptides (Peptides 1-4 (SEQ ID NOS: 3 to 6) in Table 1 and FIG. 5A) were selected on the basis of a bioinformatics analysis of V2 sequences from the LANL HIV Database. Peptide 1 (SEQ ID NO: 3) was derived from the V2 of a strain with the highest number of polar amino acids (subtype A strain QB585.2102M.Ev1v5.C from Kenya); this V2 was 38 amino acids in length. Since V2 is most frequently 40 amino acids in length (Zolla-Pazner et al., "Structure-Function Relationships of HIV-1 Envelope Sequence-Variable Regions Provide a Paradigm for Vaccine Design. *Nat. Rev Immunol.* 10:527-535 (2010), which is hereby incorporated by reference in its entirety), further analyses identified sequences from viruses containing V2 regions 40 amino acids long: Peptide 2 (SEQ ID NO: 4) represents the central 21 amino acids of V2 in the most common naturally occurring sequence (derived from subtype B strain 878v3_2475). Peptide 3 (SEQ ID NO: 5) is the V2 with the highest number of polar amino acids (from subtype A strain 01TZA341). Peptide 4 (SEQ ID NO: 6) is the consensus V2 sequence among all viruses with V2 regions of 40 amino acids.

Figure 6:
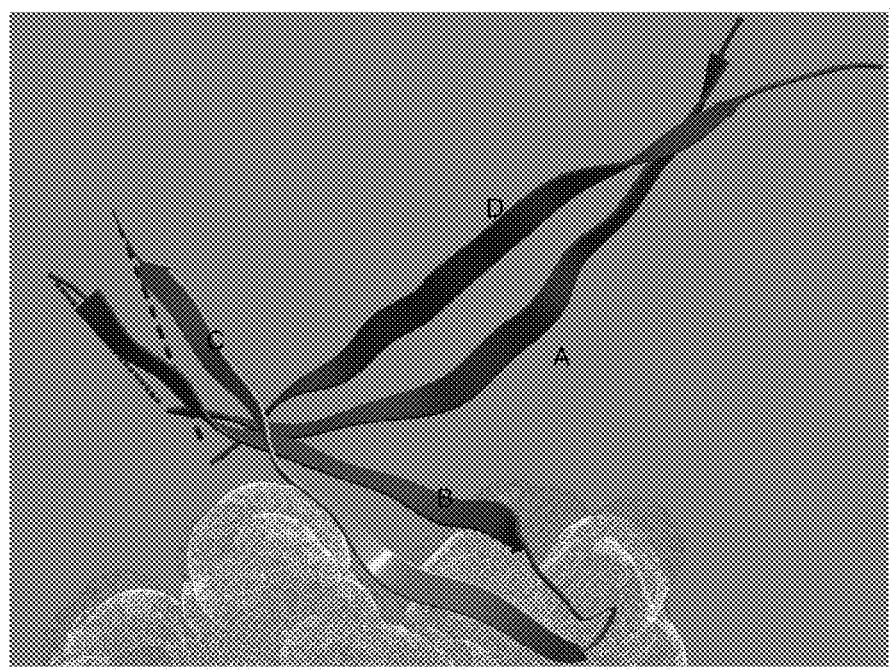
FIG. 6 shows a ribbon diagram of the backbone fold of the V1V2 domain bound to the CDR H3 loop of monoclonal antibody PG9 (transparent stippled spheres are the atoms of the PG9 CDR H3). The ribbon backbones of amino acids 165-176 are identical to Peptide 6 (SEQ ID NO: 7), is labeled C. The strands are labeled A-D according to the convention established recently (McLellan et al., "Structure of HIV-1 gp120 V1/V2 Domain With Broadly Neutralizing Antibody PG9," *Nature* 480:336-343 (2011), which is hereby incorporated by reference in its entirety).

As illustrated by the ELISA data (FIG. 5A), Peptide 1 (SEQ ID NO: 3) was the most reactive with plasma from the RV144 vaccines: 61% of plasma showed positive reactivity, i.e., had OD values above the cut-off which was based on the mean+3 SD of control plasma (from placebo recipients). Peptide 3 (SEQ ID NO: 5) was also reactive (49% positive), while Peptides 2 (SEQ ID NO: 4) and 4 (SEQ ID NO: 6) were poorly reactive (0% and 7% positive, respectively). Three overlapping peptides (Peptides 6-8 (SEQ ID NOS: 7 to 9)) were synthesized based on the sequence of the most strongly reactive Peptide 1 (SEQ ID NO: 3). Results with the overlapping peptides showed that the epitope maps to the 14 residues in Peptide 6 (SEQ ID NO: 7) containing amino acids 165-178 (FIG. 5A). The residues in this V2 region form the outer C strand of the β-sheet folded domain of VV2 (FIG. 6) (McLellan et al., "Structure of HIV-1 gp120 V1/V2 Domain With Broadly Neutralizing Antibody PG9," *Nature* 480:336-343 (2011), which is hereby incorporated by reference in its entirety).

To distinguish the amino acids that play a critical role in determining anti-V2 antibody reactivity, a further series of peptides was designed. Results with these peptides indicated that L165I (Peptide 17 (SEQ ID NO: 11)) and S174A (Peptide 20 (SEQ ID NO: 14)) replacements had little effect on reactivity (FIG. 5B). In contrast, the K169V (Peptide 18 (SEQ ID NO: 12)) and the V172E (Peptide 19 (SEQ ID NO: 13)) replacements profoundly reduced the reactivity of the plasma, indicating that these two residues are critical for binding of V2 peptides by the vaccine-induced antibodies. These data acquire enhanced importance in light of results showing that (a) sieve analysis showed that a residue other than K at position 169 was more frequent in breakthrough viruses in vaccine recipients (Rolland et al., "Sequence Analysis of HIV-1 Breakthrough Infections in the RV144 Trial. Characterization of Breakthrough Viruses," *Sequence Analysis of HIV-1 Breakthrough Infections in the RV144 Trial, Abstract S07.02* S07.02 (2011) and Edlefsen et al., "Sieve Analysis of RV144," *Abstract S07.04* S07.04 (2011), each of which is hereby incorporated by reference in its entirety), as well as (b) Gln (E) strongly predominates in subtype E whereas valine (V) slightly predominates at position 172 in subtype B. Notably, the poor response to Peptide 19 (SEQ ID NO: 13), in which the V172E mutation appears, suggests that the V2 antibody response was induced by the subtype E (A244) gp120 boosting immunogen rather than the subtype B (MN) immunogen.

Example 4

Comparison of V2 Assays Run in the Case-Control Study

Based on the pilot studies, six assay types were chosen for measuring 13 variables with case-control specimens (Table 2). One of these (ELISA binding to gp70-V1V2) was chosen as a primary variable. The secondary variables provided by the 12 additional V2 assays were run in exploratory analyses with case-control specimens. The primary and secondary variables were chosen to represent assays whose results did not correlate with one another. The heat map in FIG. 3 represents the Spearman rank correlations between the V2 assays, and demonstrates that the primary variable, binding of IgG antibodies to gp70-V1V2, correlated only weakly with ELISA binding to cyclic V2 (amino acids 157-198) (Spearman correlation: 0.5-0.6). Analysis of the microarray "hotspot" data was not performed until after completion of the analysis of the initial pilot and case-control studies. Interestingly, the V2 hotspot variable correlates poorly with all of the other V2 variables.

Figure 7:
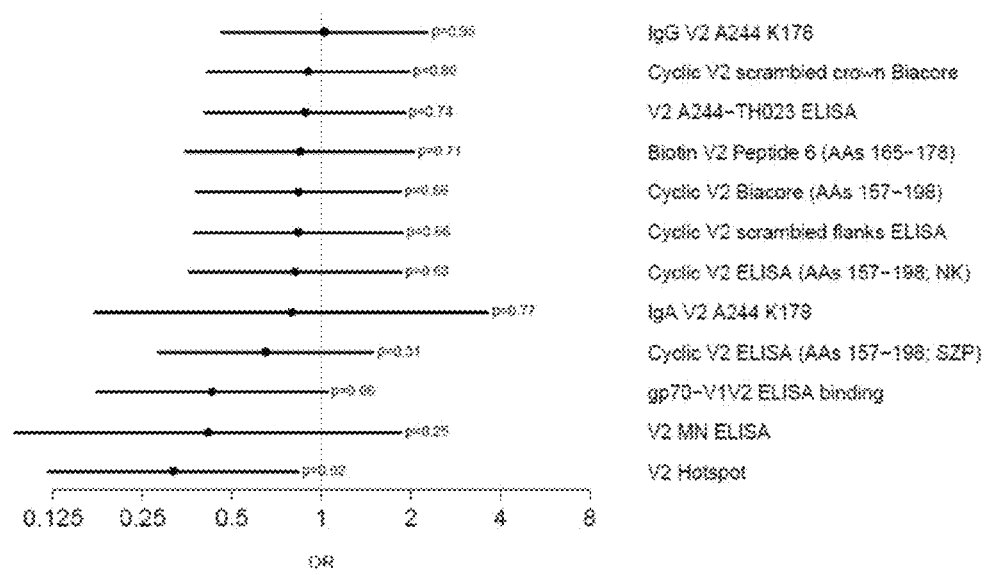
FIG. 7 shows estimated odds ratios (ORs) and 95% confidence intervals for each of the V2 assays. Data are derived from the categorical analyses shown in Table 2. Estimated ORs compare subgroups defined by high vs. low responses except for comparisons for analyses of IgA V2 A244 K178 and V2 MN which compare positive vs. negative responses. For evaluation of biotinylated V2 peptide 6 (SEQ ID NO: 7), comparison is between high and negative responses.
Figure 8:
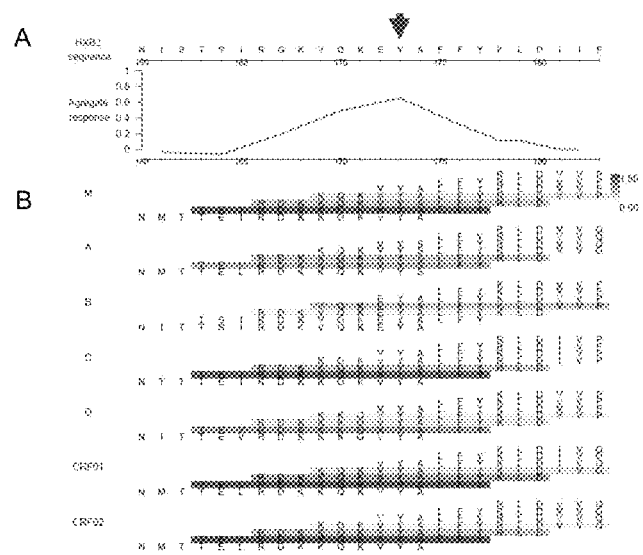
FIGS. 8A-B show microarray analysis of the V2 antibody response in plasma from vaccines in the case-control study.

For the univariate analysis, as in the multivariate analysis (Haynes et al., "Immune Correlates Analysis of the ALVAC-AIDSVAX HIV-1 Vaccine Efficacy Trial," *N Engl J Med.* 366:1275-1286 (2012), which is hereby incorporated by reference in its entirety), statistical significance was approached or achieved with the primary variable of ELISA binding to gp70-V1V2 (p=0.06 and p=0.02, respectively). With one of the secondary variables (V2 hotspot), significance was achieved (p=0.03 quantitative, and p=0.02 categorical, Table 2). The ORs calculated for each V2 variable are shown in FIG. 7 and Table 2. The univariate ORs for all V2 variables were ≤1.02, compatible with the hypothesis that V2 antibodies played a role in reducing infection. When binding antibodies were assessed by peptide microarray analysis using linear overlapping peptides covering the entire V2 region of seven major genetic subtypes, the lowest and most statistically significant OR was achieved (FIG. 7 and Table 2). The results are shown in FIG. 8 for V2 residues 160-183. Most of the remaining C-terminal portion of V2 is poorly immunogenic (Zolla-Pazner et al., "Structure-Function Relationships of HIV-1 Envelope Sequence-Variable Regions Provide a Paradigm for Vaccine Design," *Nat Rev Immunol.* 10:527-535 (2010), which is hereby incorporated by reference in its entirety), and similarly, there was little or no reactivity with peptides in the V1 region. The aggregate response (FIG. 8A), shows that the V2 response is centered around residue $K^{173}$. The peptides with the strongest reactivity encompass residues 163-177 (FIG. 8B), which matches the results from the independent ELISA data described above. It is also noteworthy that the weakest reactivity in the microarray analysis was detected with the subtype B subset of V2 peptides, confirming the poor reactivity with Peptide 19 (SEQ ID NO: 13) (FIG. 5B) which represents a canonical subtype B V2 containing a Glu (E) at position 172. Interestingly, the reactivity with the V2 peptide representing the sequence of vaccine strain MN (subtype B) also includes $E^{172}$. Only 24 of 246 vaccines' specimens reacted with the V2 MN peptide, again confirming the poor reactivity with the subtype B V2; however, strikingly, none of these 24 vaccines were infected, resulting in an OR for positive vs. negative responders of 0.41 (Table 2 and FIG. 7). The 0.25 p-value reflects the low power of these data due to the very few positive responders and could also be due to poor sensitivity of the assay since the results were reported as endpoint titers after a starting dilution of 1:30.

Discussion of Examples 1-4

In this study, the results achieved with the entire panel of V2 assays used in the RV144 pilot and case-control studies were probed in order to understand more fully the nature of the V2 antibody response and why the high response to epitopes in this region is associated with a lower rate of infection in vaccines. The data presented include all of the data describing the V2 antibodies induced by the vaccine and available from both the pilot and the case-control specimens.

These studies document at least two types of V2 antibodies induced by the RV144 vaccine: antibodies reactive with a scaffolded V1V2 protein, gp70-V1V2, and antibodies specific for linear V2 peptides. Studies with human monoclonal antibodies suggest that these may be non-overlapping antibody populations since monoclonal antibodies such as 697D and 2158 react with conformational V1V2 epitope(s) carried by gp70-V1V2 but not with linear peptides (Gorny et al., "Functional and Immunochemical Cross-Reactivity of V2-Specific Monoclonal Antibodies From Human Immunodeficiency Virus Type 1-Infected Individuals," *Virology* 427: 198-207 (2012); Gorny et al., "Human Anti-V2 Monoclonal Antibody That Neutralizes Primary but Not Laboratory Isolates of HIV-1," *J Virol.* 68:8312-8320 (1994), each of which is hereby incorporated by reference in its entirety), while monoclonal antibodies such as CH58 and CH59 react with linear V2 peptides but not with gp70-V1V2. The primary variable that correlated with reduced risk of infection measured antibody activity in ELISA with gp70-V1V2. This reagent retains a conformation presented in vivo during infection since it is recognized by antibodies in sera of infected individuals and was used for the selection of two monoclonal antibody-producing hybridomas from the cells of HIV-infected individuals which are broadly cross-reactive with diverse envelopes and neutralize several Tier 1 pseudoviruses (Gorny et al., "Functional and Immunochemical Cross-Reactivity of V2-Specific Monoclonal Antibodies From Human Immunodeficiency Virus Type 1-Infected Individuals," *Virology* 427:198-207 (2012); Pinter et al., "The V1/V2 Domain of gp120 is a Global Regulator of Sensitivity of Primary Human Immunodeficiency Virus Type I Isoloates to Neutralization by Antibodies Commonly Induced Upon Infection," *J Virol.* 78:5205-5215 (2004), each of which is hereby incorporated by reference in its entirety).

The reactivity of vaccines' antibodies with overlapping V2 peptides also correlated with reduced risk of infection (Table 2), generating the hypothesis that antibodies to linear V2 epitopes were also involved in reducing the rate of HIV infection. The observation that none of the vaccines who produced antibodies reactive with the linear subtype B MN V2 peptide were infected with HIV during the trial is intriguing, although the low power of the result reduces confidence in the significance of this observation. The data generated with various linear V2 peptides indicate that: (a) the dominant immunogenic linear V2 epitope in the RV144 vaccine encompasses residues 165 to 178; (b) the V2 antibodies were induced primarily by subtype E A244 rather than the subtype B MN gp120 boost; (c) the V2 antibodies were cross-reactive with V2 peptides derived from several subtypes, (d) the dominant linear V2 epitope was located in the C β-strand of the V1V2 complex (FIG. 6 and McLellan et al., "Structure of HIV-1 gp120 V1/V2 Domain With Broadly Neutralizing Antibody PG9" *Nature* 480: 336-343 (2011), which is hereby incorporated by reference in its entirety), (e) residues $K^{169}$ and $V^{172}$, were critical for the binding of vaccines' plasma antibodies to V2 peptides, and (f) the V2 epitope includes the lysine at position 169 which was identified by sieve analysis to be mismatched in breakthrough infections (Rolland et al., "Sequence Analysis of HIV-1 Breakthrough Infections in the RV144 Trial. Characterization of Breakthrough Viruses," *Sequence Analysis of HIV-1 Breakthrough Infections in the RV144 Trial, Abstract S07.02* S07.02 (2011), which is hereby incorporated by reference in its entirety).

It is noteworthy that the single primary variable showing an inverse correlate of infection risk in the RV144 case-control study was antibody reactivity with gp70-V1V2 which contains the V1V2 sequence of case A2, a subtype B strain (Pinter et al., "Potent Neutralization of Primary HIV-1 Isolates by Antibodies Directed Against Epitopes Present in the V1/V2 Domain of HIV-1 gp120," *Vaccine* 16:1803-1811 (1998), which is hereby incorporated by reference in its entirety) which carries both the V169 and the E172 residues that reduce reactivity of vaccines' antibodies with V2 peptides. Notably, however, as shown above, vaccines' plasma do react with subtype B-derived linear V2 peptides, though with less potent and less frequent reactivity than with V2 peptides from other subtypes. The data with gp70-V1V2 and the linear peptides may suggest that the effective antibody populations are those which are broadly cross-reactive, targeting conformational and linear epitopes shared by diverse HIV-1 subtypes. Indeed, these data, together with bioinformatics data on V2 (Zolla-Pazner et al., "Structure-Function Relationships of HIV-1 Envelope Sequence-Variable Regions Provide a Paradigm for Vaccine Design," *Nat Rev Immunol.* 10:527-535 (2010), which is hereby incorporated by reference in its entirety) and studies of the preferential gene usage of VH families by V2-specific monoclonal antibodies (Gorny et al., "Functional and Immunochemical Cross-Reactivity of V2-Specific Monoclonal Antibodies From Human Immunodeficiency Virus Type 1-Infected Individuals," *Virology* 427:198-207 (2012), which is hereby incorporated by reference in its entirety), support the presence of conserved and immunologically cross-reactive elements in the V2 loop. The role of shared structures and antigenic determinants in the variable loops of the envelope in inducing potentially protective antibody responses is also suggested by the involvement of the V2 and V3 loops as components of the epitopes recognized by the class of potently neutralizing antibodies that target quaternary epitopes and proteoglycans on the envelope spike (Gomy et al., "Identification of a New Quaternary Neutralizing Epitope on Human Immunodeficiency Virus Type I Virus Particles," *J. Virol.* 79:5232-5237 (2005); Walker et al., "Broad and Potent Neutralizing Antibodies From an African Donor Reveal a New HIV-1 Vaccine Target," *Science* 326: 285-289 (2009); Changela et al., "Crystal Structure of Human Antibody 2909 Reveals Conserved Features of Quaternary-Specific Antibodies that Potentially Neutralize HIV-1," *J Virol.* 85:2524-2535 (2011); Spurrier et al., "Structural Analysis and Computational Modeling of Human and Macaque Monoclonal Antibodies Provide a Model for the Quaternary Neutralizing Epitope of HIV-1 gp120," *Structure* 19:691-699 (2011); Wu et al., "Immunotypes of a Quaternary Structure of the HIV-1 Envelope Affect Viral Vulnerability to Neutralizing Antibodies," *J. Virol.* 85:4578-4585 (2011); Bonsignori et al., "Analysis of a Clonal Lineage of HIV-1 Envelope V2/V3 Comformational Epitope-Specific Broadly Neutralizing Antibodies and Their Inferred Unmutated Common Ancestors," *Journal of Virology* 85:9998-10009 (2011); Walker at al., "Broad Neutralization Coverage of HIV by Multiple Highly Potent Antibodies," *Nature* 477:466-470 (2011); Pejchal et al., "A Potent and Broad Neutralizing Antibody Recognizes and Penetrates the HIV Glycan Shield," *Science* 334:1097-1103 (2011), each of which is hereby incorporated by reference in its entirety).

The explanation for the strong induction of V2 antibodies by the A244 subtype E gp120 immunogen compared to the weak response induced by the MN subtype B gp120 despite the similar antigenicity of the two proteins has several possible explanations. It may be due to a proteolytic cleavage site in the V2 loop of MN; a cathepsin D cleavage site (QKEYALL (SEQ ID NO: 75)) exists in the V2 of MN (Yu et al., "Protease Cleavage Sites in HIV-1 gp120 Recognized by Antigen Processing Enzymes are Conserved and Located at Receptor Binding Sites," *J. Virol.* 84:1513-1526 (2010), which is hereby incorporated by reference in its entirety), while this site is absent from the V2 of A244 (QKVHALF (SEQ ID NO: 76)). The importance of proteoloysis by lysosomal enzymes on antigen presentation and induction of immune responses to gp120 was previously described (Chien et al., "Human Immunodeficiency Virus Type I Evades T-helper Responses by Expoiting Antibodies that Suppress Antigen Processing," *J. Virol.* 78:7645-7652 (2004), which is hereby incorporated by reference in its entirety), providing a theoretical explanation for understanding the differential antibody responses to these two gp120 immunogens. Alternatively, the immunogenicity of the V2 in the MN gp120 boosting immunogen may be less than that of the A244 immunogen, and/or the subtype E rather than the subtype B V2 region is the greater similarity of the AIDSVAX subtype E gp120 protein boost to the subtype E Env used in the prime. To address these issues, further studies of V2 responses with specimens from other vaccine trials, e.g., VAX003 and VAX004, are underway, along with assays using additional peptides, proteoglycans, and epitope-scaffolded proteins.

Finally, the mechanisms by which anti-V2 antibodies may reduce HIV infection have yet to be understood. As noted, anti-V2 monoclonal antibodies can neutralize many Tier 1 pseudoviruses in the TZM.bl assay (Gorny et al., "Functional and Immunochemical Cross-Reactivity of V2-Specific Monoclonal Antibodies From Human Immunodeficiency Virus Type 1-Infected Individuals," *Virology* 427: 198-207 (2012), which is hereby incorporated by reference in its entirety). It is possible that they mediate broader neutralizing activity than is detected in this particular assay. Plasma samples from RV144 neutralized some Tier 1 viruses in the TZM-bl assay and in a more sensitive assay with A3R5 cells; however no neutralization of Tier 2 viruses was detected in either assay. Since V2 can be detected on the surface of virions (Nyambi et al., "Conserved and Exposed Epitopes on Intact, Native, Primary Human Immunodeficiency Virus Type I Virions of Group M," *J. Virol.* 74:7096-7107 (2000), which is hereby incorporated by reference in its entirety) and infected cells (Zolla-Pazner et al., "Serotyping of Primary Human Immunodeficiency Virus Type I Isolates From Diverse Geographic Locations by Flow Cytometry," *J. Virol.* 69:3807-3815 (1995), which is hereby incorporated by reference in its entirety), these antibodies may also mediate various other anti-viral functions such as ADCC, ADCVI, virolysis, virus opsonization, virus aggregation, etc. Along with current studies of the potential biologic functions of V2 antibodies, assessment is on-going to test several hypotheses, including those that postulate that anti-V2 antibodies prevent conformational changes in the envelope necessary for binding to CCR5, and that these antibodies may, or may not, prevent binding of the envelope to α4β7. Interestingly, after vaccination of non-human primates with Ad26 and MVA containing SIVsm543 inserts, a low dose intra-rectal heterologous SIVmac251 challenge identified a potential V2 correlate of protection (Barouch et al., "Vaccine Protection Against Acquisition of Neutralization-Resistant SIV Challenges in Rhesus Monkeys," *Nature* 482:89-93 (2012), which is hereby incorporated by reference in its entirety). While the relevance of the SIV model to ALVAC-HIV and AIDSVAX B/E responses in humans may be unclear, the presence of this analogous protective response after vaccination, in addition to the results of the RV144 immune correlates analysis, may provide a means to illuminate the postulated mechanism for reducing the risk of infection.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. An isolated, cyclized immunogenic peptide consisting of the amino acid sequence of SEQ ID NO:1.

2. The isolated immunogenic peptide of claim 1, wherein the peptide consists of the amino acid sequence of SEQ ID NO: 7.

3. The isolated immunogenic peptide of claim 1, wherein the peptide consists of the amino acid sequence of SEQ ID NO: 11.

4. The isolated immunogenic peptide of claim 1, wherein the peptide consists of the amino acid sequence of SEQ ID NO: 12.

5. The isolated immunogenic peptide of claim 1, wherein the peptide consists of the amino acid sequence of SEQ ID NO: 13.

6. The isolated immunogenic peptide of claim 1, wherein the peptide consists of the amino acid sequence of SEQ ID NO: 14.

7. The isolated immunogenic peptide of claim 1, wherein the peptide consists of the amino acid sequence of SEQ ID NO: 16.

8. An immunogenic composition comprising:

the cyclized immunogenic peptide of claim 1 and an immunologically and pharmaceutically acceptable vehicle or excipient.

9. The immunogenic composition of claim 8 further comprising:

an adjuvant or immunostimulatory peptide or polypeptide that is different from said immunogenic polypeptide.

10. The immunogenic composition of claim 9, wherein said immunostimulatory polypeptide is a cytokine.

11. The immunogenic composition of claim 9, wherein the adjuvant is selected from the group consisting of: (a) ISAF-1 (5% squalene, 2.5% pluronic L121, 0.2% Tween 80) in phosphate buffered solution with 0.4 mg of threonyl-muramyl dipeptide; (b) de-oiled lecithin dissolved in an oil; (c) aluminum hydroxide gel; (d) a mixture of (b) and (c); (e) QS-21; (f) monophosphoryl lipid A adjuvant; and (g) incomplete Freund's adjuvant.

* * * * *

UNITED STATES PATENT AND TRADEMARK OFFICE
CERTIFICATE OF CORRECTION

PATENT NO. : 9,611,294 B2  
APPLICATION NO. : 13/612300  
DATED : April 4, 2017  
INVENTOR(S) : Cardozo et al.

Page 1 of 1

It is certified that error appears in the above-identified patent and that said Letters Patent is hereby corrected as shown below:

In the Specification

Column 1 at Lines 9-12, delete "The subject matter of this application was made with support from the United States National Institutes of Health Grant No. R01-A1084119. The U.S. government has certain rights in the invention." and insert --This invention was made with government support under R01 AI084119 awarded by National Institutes of Health. The government has certain rights in the invention.--

Signed and Sealed this
Twenty-first Day of August, 2018

Andrei Iancu
*Director of the United States Patent and Trademark Office*

SEQUENCE LISTING

```
<160> NUMBER OF SEQ ID NOS: 76

<210> SEQ ID NO 1
<211> LENGTH: 14
<212> TYPE: PRT
<213> ORGANISM: Artificial Sequence
```

```
<220> FEATURE:
<223> OTHER INFORMATION: consensus peptide from V2 loop of HIV gp120
<220> FEATURE:
<221> NAME/KEY: MISC_FEATURE
<222> LOCATION: (1)..(1)
<223> OTHER INFORMATION: Xaa at position 1 is L, V, I, M, F, W or A
<220> FEATURE:
<221> NAME/KEY: MISC_FEATURE
<222> LOCATION: (2)..(2)
<223> OTHER INFORMATION: Xaa at position 2 is any amino acid
<220> FEATURE:
<221> NAME/KEY: MISC_FEATURE
<222> LOCATION: (4)..(4)
<223> OTHER INFORMATION: Xaa at position 4 is R, K or H
<220> FEATURE:
<221> NAME/KEY: MISC_FEATURE
<222> LOCATION: (5)..(5)
<223> OTHER INFORMATION: Xaa at position 5 is K, D, E, R, H, S, T, C, N,
     Q, Y, A, V or M
<220> FEATURE:
<221> NAME/KEY: MISC_FEATURE
<222> LOCATION: (6)..(6)
<223> OTHER INFORMATION: Xaa at position 6 is K, D, E, R, H, S, T, C, N,
     Q, Y or A
<220> FEATURE:
<221> NAME/KEY: MISC_FEATURE
<222> LOCATION: (7)..(7)
<223> OTHER INFORMATION: Xaa at position 7 is K, D, E, R, H, S, T, C, N,
     Q, Y or A
<220> FEATURE:
<221> NAME/KEY: MISC_FEATURE
<222> LOCATION: (8)..(8)
<223> OTHER INFORMATION: Xaa at position 8 is L, V, I, M, F, W, A or E
<220> FEATURE:
<221> NAME/KEY: MISC_FEATURE
<222> LOCATION: (10)..(10)
<223> OTHER INFORMATION: Xaa at position 10 is K, D, E, R, H, S, T, C,
     N, Q, Y or A
<220> FEATURE:
<221> NAME/KEY: MISC_FEATURE
<222> LOCATION: (11)..(11)
<223> OTHER INFORMATION: Xaa at position 11 is L, V, I, M, F, W or A
<220> FEATURE:
<221> NAME/KEY: MISC_FEATURE
<222> LOCATION: (12)..(12)
<223> OTHER INFORMATION: Xaa at position 12 is F or T
<220> FEATURE:
<221> NAME/KEY: MISC_FEATURE
<222> LOCATION: (13)..(13)
<223> OTHER INFORMATION: Xaa at position 13 is K, D, E, R, H, S, T, C,
     N, Q, Y or A
<220> FEATURE:
<221> NAME/KEY: MISC_FEATURE
<222> LOCATION: (14)..(14)
<223> OTHER INFORMATION: Xaa at position 14 is K, D, E, R, H, S, T, C,
     N, Q, Y or A

<400> SEQUENCE: 1

Xaa Xaa Asp Xaa Xaa Xaa Xaa Xaa Tyr Xaa Xaa Xaa Xaa Xaa
1               5                   10

<210> SEQ ID NO 2
<211> LENGTH: 14
<212> TYPE: PRT
<213> ORGANISM: Artificial Sequence
<220> FEATURE:
<223> OTHER INFORMATION: consensus peptide from V2 loop of HIV gp120
<220> FEATURE:
<221> NAME/KEY: MISC_FEATURE
<222> LOCATION: (1)..(1)
<223> OTHER INFORMATION: Xaa at position 1 is L, V, I, M, F, W or A
<220> FEATURE:
<221> NAME/KEY: MISC_FEATURE
<222> LOCATION: (2)..(2)
<223> OTHER INFORMATION: Xaa at position 2 is any amino acid
<220> FEATURE:
<221> NAME/KEY: MISC_FEATURE
```

```
<222> LOCATION: (4)..(4)
<223> OTHER INFORMATION: Xaa at position 4 is R, K or H
<220> FEATURE:
<221> NAME/KEY: MISC_FEATURE
<222> LOCATION: (5)..(5)
<223> OTHER INFORMATION: Xaa at position 5 is K, D, E, R, H, S, T, C, N,
      Q, Y, A, V or M
<220> FEATURE:
<221> NAME/KEY: MISC_FEATURE
<222> LOCATION: (6)..(6)
<223> OTHER INFORMATION: Xaa at position 6 is K, D, E, R, H, S, T, C, N,
      Q, Y or A
<220> FEATURE:
<221> NAME/KEY: MISC_FEATURE
<222> LOCATION: (7)..(7)
<223> OTHER INFORMATION: Xaa at position 7 is K, D, E, R, H, S, T, C, N,
      Q, Y or A
<220> FEATURE:
<221> NAME/KEY: MISC_FEATURE
<222> LOCATION: (8)..(8)
<223> OTHER INFORMATION: Xaa at position 8 is L, V, I, M, F, W, A or E
<220> FEATURE:
<221> NAME/KEY: MISC_FEATURE
<222> LOCATION: (10)..(10)
<223> OTHER INFORMATION: Xaa at position 10 is K, D, E, R, H, S, T, C,
      N, Q, Y or A
<220> FEATURE:
<221> NAME/KEY: MISC_FEATURE
<222> LOCATION: (11)..(11)
<223> OTHER INFORMATION: Xaa at position 11 is L, V, I, M, F, W or A
<220> FEATURE:
<221> NAME/KEY: MISC_FEATURE
<222> LOCATION: (12)..(12)
<223> OTHER INFORMATION: Xaa at position 12 is F or T
<220> FEATURE:
<221> NAME/KEY: MISC_FEATURE
<222> LOCATION: (13)..(13)
<223> OTHER INFORMATION: Xaa at position 13 is is any amino acid other
      than Y
<220> FEATURE:
<221> NAME/KEY: MISC_FEATURE
<222> LOCATION: (14)..(14)
<223> OTHER INFORMATION: Xaa at position 14 is K, D, E, R, H, S, T, C,
      N, Q, Y or A

<400> SEQUENCE: 2

Xaa Xaa Asp Xaa Xaa Xaa Xaa Xaa Tyr Xaa Xaa Xaa Xaa Xaa
1               5                   10

<210> SEQ ID NO 3
<211> LENGTH: 21
<212> TYPE: PRT
<213> ORGANISM: Artificial Sequence
<220> FEATURE:
<223> OTHER INFORMATION: peptide of most polar V2 sequence from HIV
      gp120

<400> SEQUENCE: 3

Leu Arg Asp Lys Lys Gln Arg Val Tyr Ser Leu Phe Tyr Lys Leu Asp
1               5                   10                  15

Val Val Gln Ile Asn
            20

<210> SEQ ID NO 4
<211> LENGTH: 21
<212> TYPE: PRT
<213> ORGANISM: Artificial Sequence
<220> FEATURE:
<223> OTHER INFORMATION: peptide of most common 40 amino acid V2
      sequence from HIV gp120

<400> SEQUENCE: 4

Ile Arg Asp Lys Val Gln Lys Glu Tyr Ala Leu Phe Tyr Lys Leu Asp
```

```
                    1               5                   10                  15

Val Val Pro Ile Asp
            20

<210> SEQ ID NO 5
<211> LENGTH: 21
<212> TYPE: PRT
<213> ORGANISM: Artificial Sequence
<220> FEATURE:
<223> OTHER INFORMATION: peptide of most polar 40 amino acid V2 sequence
      from HIV gp120

<400> SEQUENCE: 5

Leu Arg Asp Lys Lys Gln Gln Val Tyr Ser Leu Phe Tyr Arg Leu Asp
1               5                   10                  15

Ile Glu Lys Ile Asn
            20

<210> SEQ ID NO 6
<211> LENGTH: 21
<212> TYPE: PRT
<213> ORGANISM: Artificial Sequence
<220> FEATURE:
<223> OTHER INFORMATION: consensus peptide of 40 amino acid V2 sequence
      from HIV gp120

<400> SEQUENCE: 6

Ile Arg Asp Lys Lys Gln Lys Glu Tyr Ala Leu Phe Tyr Lys Leu Asp
1               5                   10                  15

Val Val Pro Ile Asp
            20

<210> SEQ ID NO 7
<211> LENGTH: 14
<212> TYPE: PRT
<213> ORGANISM: Artificial Sequence
<220> FEATURE:
<223> OTHER INFORMATION: peptide of first 14 amino acids of SEQ ID NO: 3

<400> SEQUENCE: 7

Leu Arg Asp Lys Lys Gln Arg Val Tyr Ser Leu Phe Tyr Lys
1               5                   10

<210> SEQ ID NO 8
<211> LENGTH: 14
<212> TYPE: PRT
<213> ORGANISM: Artificial Sequence
<220> FEATURE:
<223> OTHER INFORMATION: peptide of central 14-mer of SEQ ID NO: 3

<400> SEQUENCE: 8

Lys Gln Arg Val Tyr Ser Leu Phe Tyr Lys Leu Asp Val Val
1               5                   10

<210> SEQ ID NO 9
<211> LENGTH: 13
<212> TYPE: PRT
<213> ORGANISM: Artificial Sequence
<220> FEATURE:
<223> OTHER INFORMATION: peptide of C-terminal 13-mer of SEQ ID NO: 3

<400> SEQUENCE: 9

Tyr Ser Leu Phe Tyr Lys Leu Asp Val Val Gln Ile Asn
1               5                   10
```

<210> SEQ ID NO 10
<211> LENGTH: 17
<212> TYPE: PRT
<213> ORGANISM: Artificial Sequence
<220> FEATURE:
<223> OTHER INFORMATION: peptide of SEQ ID NO: 7 with N-terminal glycines

<400> SEQUENCE: 10

Gly Gly Gly Leu Arg Asp Lys Lys Gln Arg Val Tyr Ser Leu Phe Tyr
1               5                   10                  15
Lys

<210> SEQ ID NO 11
<211> LENGTH: 17
<212> TYPE: PRT
<213> ORGANISM: Artificial Sequence
<220> FEATURE:
<223> OTHER INFORMATION: peptide of SEQ ID NO: 7 with L165I mutation

<400> SEQUENCE: 11

Gly Gly Gly Ile Arg Asp Lys Lys Gln Arg Val Tyr Ser Leu Phe Tyr
1               5                   10                  15
Lys

<210> SEQ ID NO 12
<211> LENGTH: 17
<212> TYPE: PRT
<213> ORGANISM: Artificial Sequence
<220> FEATURE:
<223> OTHER INFORMATION: peptide of SEQ ID NO: 7 with K169V mutation

<400> SEQUENCE: 12

Gly Gly Gly Leu Arg Asp Lys Val Gln Arg Val Tyr Ser Leu Phe Tyr
1               5                   10                  15
Lys

<210> SEQ ID NO 13
<211> LENGTH: 17
<212> TYPE: PRT
<213> ORGANISM: Artificial Sequence
<220> FEATURE:
<223> OTHER INFORMATION: peptide of SEQ ID NO: 7 with V172E mutation

<400> SEQUENCE: 13

Gly Gly Gly Leu Arg Asp Lys Lys Gln Arg Glu Tyr Ser Leu Phe Tyr
1               5                   10                  15
Lys

<210> SEQ ID NO 14
<211> LENGTH: 17
<212> TYPE: PRT
<213> ORGANISM: Artificial Sequence
<220> FEATURE:
<223> OTHER INFORMATION: peptide of SEQ ID NO: 7 with S174A mutation

<400> SEQUENCE: 14

Gly Gly Gly Leu Arg Asp Lys Lys Gln Arg Val Tyr Ala Leu Phe Tyr
1               5                   10                  15
Lys

<210> SEQ ID NO 15
<211> LENGTH: 14
<212> TYPE: PRT

```
<213> ORGANISM: Artificial Sequence
<220> FEATURE:
<223> OTHER INFORMATION: peptide from V2 loop of HIV gp120

<400> SEQUENCE: 15

Leu Gln Asn Lys Lys Gln Gln Val Tyr Ser Leu Phe Tyr Gln
1               5                   10

<210> SEQ ID NO 16
<211> LENGTH: 14
<212> TYPE: PRT
<213> ORGANISM: Artificial Sequence
<220> FEATURE:
<223> OTHER INFORMATION: peptide of SEQ ID NO: 1 which requires Y at
      position 11

<400> SEQUENCE: 16

Leu Arg Asp Lys Met Gln Lys Val Tyr Ala Leu Thr Tyr Lys
1               5                   10

<210> SEQ ID NO 17
<211> LENGTH: 6
<212> TYPE: PRT
<213> ORGANISM: Artificial Sequence
<220> FEATURE:
<223> OTHER INFORMATION: peptide of consensus V2 region of HIV-1 Group M

<400> SEQUENCE: 17

Arg Leu Asp Val Val Pro
1               5

<210> SEQ ID NO 18
<211> LENGTH: 9
<212> TYPE: PRT
<213> ORGANISM: Artificial Sequence
<220> FEATURE:
<223> OTHER INFORMATION: peptide of consensus V2 region of HIV-1 Group M

<400> SEQUENCE: 18

Leu Phe Tyr Arg Leu Asp Val Val Pro
1               5

<210> SEQ ID NO 19
<211> LENGTH: 12
<212> TYPE: PRT
<213> ORGANISM: Artificial Sequence
<220> FEATURE:
<223> OTHER INFORMATION: peptide of consensus V2 region of HIV-1 Group M

<400> SEQUENCE: 19

Val Tyr Ala Leu Phe Tyr Arg Leu Asp Val Val Pro
1               5                   10

<210> SEQ ID NO 20
<211> LENGTH: 15
<212> TYPE: PRT
<213> ORGANISM: Artificial Sequence
<220> FEATURE:
<223> OTHER INFORMATION: peptide of consensus V2 region of HIV-1 Group M

<400> SEQUENCE: 20

Lys Gln Lys Val Tyr Ala Leu Phe Tyr Arg Leu Asp Val Val Pro
1               5                   10                  15

<210> SEQ ID NO 21
<211> LENGTH: 15
<212> TYPE: PRT
```

-continued

```
<213> ORGANISM: Artificial Sequence
<220> FEATURE:
<223> OTHER INFORMATION: peptide of consensus V2 region of HIV-1 Group M

<400> SEQUENCE: 21

Arg Asp Lys Lys Gln Lys Val Tyr Ala Leu Phe Tyr Arg Leu Asp
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: peptide of consensus V2 region of HIV-1 Group M

<400> SEQUENCE: 22

Thr Glu Ile Arg Asp Lys Lys Gln Lys Val Tyr Ala Leu Phe Tyr
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: peptide of consensus V2 region of HIV-1 Group M

<400> SEQUENCE: 23

Asn Met Thr Thr Glu Ile Arg Asp Lys Lys Gln Lys Val Tyr Ala
1               5                   10                  15

<210> SEQ ID NO 24
<211> LENGTH: 6
<212> TYPE: PRT
<213> ORGANISM: Artificial Sequence
<220> FEATURE:
<223> OTHER INFORMATION: peptide of consensus V2 region of HIV-1 subtype
      A

<400> SEQUENCE: 24

Arg Leu Asp Val Val Gln
1               5

<210> SEQ ID NO 25
<211> LENGTH: 9
<212> TYPE: PRT
<213> ORGANISM: Artificial Sequence
<220> FEATURE:
<223> OTHER INFORMATION: peptide of consensus V2 region of HIV-1 subtype
      A

<400> SEQUENCE: 25

Leu Phe Tyr Arg Leu Asp Val Val Gln
1               5

<210> SEQ ID NO 26
<211> LENGTH: 12
<212> TYPE: PRT
<213> ORGANISM: Artificial Sequence
<220> FEATURE:
<223> OTHER INFORMATION: peptide of consensus V2 region of HIV-1 subtype
      A

<400> SEQUENCE: 26

Val Tyr Ser Leu Phe Tyr Arg Leu Asp Val Val Gln
1               5                   10

<210> SEQ ID NO 27
```

```
<211> LENGTH: 15
<212> TYPE: PRT
<213> ORGANISM: Artificial Sequence
<220> FEATURE:
<223> OTHER INFORMATION: peptide of consensus V2 region of HIV-1 subtype
      A

<400> SEQUENCE: 27

Lys Gln Lys Val Tyr Ser Leu Phe Tyr Arg Leu Asp Val Val Gln
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: peptide of consensus V2 region of HIV-1 subtype
      A

<400> SEQUENCE: 28

Arg Asp Lys Lys Gln Lys Val Tyr Ser Leu Phe Tyr Arg Leu Asp
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: peptide of consensus V2 region of HIV-1 subtype
      A

<400> SEQUENCE: 29

Thr Glu Leu Arg Asp Lys Lys Gln Lys Val Tyr Ser Leu Phe Tyr
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: peptide of consensus V2 region of HIV-1 subtype
      A

<400> SEQUENCE: 30

Asn Met Thr Thr Glu Leu Arg Asp Lys Lys Gln Lys Val Tyr Ser
1               5                   10                  15

<210> SEQ ID NO 31
<211> LENGTH: 6
<212> TYPE: PRT
<213> ORGANISM: Artificial Sequence
<220> FEATURE:
<223> OTHER INFORMATION: peptide of consensus V2 region of HIV-1 subtype
      B

<400> SEQUENCE: 31

Lys Leu Asp Val Val Pro
1               5

<210> SEQ ID NO 32
<211> LENGTH: 9
<212> TYPE: PRT
<213> ORGANISM: Artificial Sequence
<220> FEATURE:
<223> OTHER INFORMATION: peptide of consensus V2 region of HIV-1 subtype
      B

<400> SEQUENCE: 32
```

```
Leu Phe Tyr Lys Leu Asp Val Val Pro
1               5
```

<210> SEQ ID NO 33
<211> LENGTH: 12
<212> TYPE: PRT
<213> ORGANISM: Artificial Sequence
<220> FEATURE:
<223> OTHER INFORMATION: peptide of consensus V2 region of HIV-1 subtype
      B

<400> SEQUENCE: 33

```
Glu Tyr Ala Leu Phe Tyr Lys Leu Asp Val Val Pro
1               5                   10
```

<210> SEQ ID NO 34
<211> LENGTH: 15
<212> TYPE: PRT
<213> ORGANISM: Artificial Sequence
<220> FEATURE:
<223> OTHER INFORMATION: peptide of consensus V2 region of HIV-1 subtype
      B

<400> SEQUENCE: 34

```
Val Gln Lys Glu Tyr Ala Leu Phe Tyr Lys Leu Asp Val Val Pro
1               5                   10                  15
```

<210> SEQ ID NO 35
<211> LENGTH: 15
<212> TYPE: PRT
<213> ORGANISM: Artificial Sequence
<220> FEATURE:
<223> OTHER INFORMATION: peptide of consensus V2 region of HIV-1 subtype
      B

<400> SEQUENCE: 35

```
Arg Asp Lys Val Gln Lys Glu Tyr Ala Leu Phe Tyr Lys Leu Asp
1               5                   10                  15
```

<210> SEQ ID NO 36
<211> LENGTH: 15
<212> TYPE: PRT
<213> ORGANISM: Artificial Sequence
<220> FEATURE:
<223> OTHER INFORMATION: peptide of consensus V2 region of HIV-1 subtype
      B

<400> SEQUENCE: 36

```
Thr Ser Ile Arg Asp Lys Val Gln Lys Glu Tyr Ala Leu Phe Tyr
1               5                   10                  15
```

<210> SEQ ID NO 37
<211> LENGTH: 15
<212> TYPE: PRT
<213> ORGANISM: Artificial Sequence
<220> FEATURE:
<223> OTHER INFORMATION: peptide of consensus V2 region of HIV-1 subtype
      B

<400> SEQUENCE: 37

```
Asn Ile Thr Thr Ser Ile Arg Asp Lys Val Gln Lys Glu Tyr Ala
1               5                   10                  15
```

<210> SEQ ID NO 38
<211> LENGTH: 6
<212> TYPE: PRT
<213> ORGANISM: Artificial Sequence
<220> FEATURE:

<223> OTHER INFORMATION: peptide of consensus V2 region of HIV-1 subtype
      C

<400> SEQUENCE: 38

Arg Leu Asp Ile Val Pro
1               5

<210> SEQ ID NO 39
<211> LENGTH: 9
<212> TYPE: PRT
<213> ORGANISM: Artificial Sequence
<220> FEATURE:
<223> OTHER INFORMATION: peptide of consensus V2 region of HIV-1 subtype
      C

<400> SEQUENCE: 39

Leu Phe Tyr Arg Leu Asp Ile Val Pro
1               5

<210> SEQ ID NO 40
<211> LENGTH: 12
<212> TYPE: PRT
<213> ORGANISM: Artificial Sequence
<220> FEATURE:
<223> OTHER INFORMATION: peptide of consensus V2 region of HIV-1 subtype
      C

<400> SEQUENCE: 40

Val Tyr Ala Leu Phe Tyr Arg Leu Asp Ile Val Pro
1               5                   10

<210> SEQ ID NO 41
<211> LENGTH: 15
<212> TYPE: PRT
<213> ORGANISM: Artificial Sequence
<220> FEATURE:
<223> OTHER INFORMATION: peptide of consensus V2 region of HIV-1 subtype
      C

<400> SEQUENCE: 41

Lys Gln Lys Val Tyr Ala Leu Phe Tyr Arg Leu Asp Ile Val Pro
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: peptide of consensus V2 region of HIV-1 subtype
      C

<400> SEQUENCE: 42

Arg Asp Lys Lys Gln Lys Val Tyr Ala Leu Phe Tyr Arg Leu Asp
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: peptide of consensus V2 region of HIV-1 subtype
      C

<400> SEQUENCE: 43

Thr Glu Ile Arg Asp Lys Lys Gln Lys Val Tyr Ala Leu Phe Tyr
1               5                   10                  15

```
<210> SEQ ID NO 44
<211> LENGTH: 15
<212> TYPE: PRT
<213> ORGANISM: Artificial Sequence
<220> FEATURE:
<223> OTHER INFORMATION: peptide of consensus V2 region of HIV-1 subtype
      C

<400> SEQUENCE: 44

Asn Thr Thr Thr Glu Ile Arg Asp Lys Lys Gln Lys Val Tyr Ala
1               5                   10                  15

<210> SEQ ID NO 45
<211> LENGTH: 6
<212> TYPE: PRT
<213> ORGANISM: Artificial Sequence
<220> FEATURE:
<223> OTHER INFORMATION: peptide of consensus V2 region of HIV-1 subtype
      D

<400> SEQUENCE: 45

Lys Leu Asp Val Val Pro
1               5

<210> SEQ ID NO 46
<211> LENGTH: 9
<212> TYPE: PRT
<213> ORGANISM: Artificial Sequence
<220> FEATURE:
<223> OTHER INFORMATION: peptide of consensus V2 region of HIV-1 subtype
      D

<400> SEQUENCE: 46

Leu Phe Tyr Lys Leu Asp Val Val Pro
1               5

<210> SEQ ID NO 47
<211> LENGTH: 12
<212> TYPE: PRT
<213> ORGANISM: Artificial Sequence
<220> FEATURE:
<223> OTHER INFORMATION: peptide of consensus V2 region of HIV-1 subtype
      D

<400> SEQUENCE: 47

Val Tyr Ala Leu Phe Tyr Lys Leu Asp Val Val Pro
1               5                   10

<210> SEQ ID NO 48
<211> LENGTH: 15
<212> TYPE: PRT
<213> ORGANISM: Artificial Sequence
<220> FEATURE:
<223> OTHER INFORMATION: peptide of consensus V2 region of HIV-1 subtype
      D

<400> SEQUENCE: 48

Lys Lys Gln Val Tyr Ala Leu Phe Tyr Lys Leu Asp Val Val Pro
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: peptide of consensus V2 region of HIV-1 subtype
      D

<400> SEQUENCE: 49
```

```
Arg Asp Lys Lys Lys Gln Val Tyr Ala Leu Phe Tyr Lys Leu Asp
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: peptide of consensus V2 region of HIV-1 subtype
      D

<400> SEQUENCE: 50

Thr Glu Val Arg Asp Lys Lys Gln Val Tyr Ala Leu Phe Tyr
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: peptide of consensus V2 region of HIV-1 subtype
      D

<400> SEQUENCE: 51

Asn Ile Thr Thr Glu Val Arg Asp Lys Lys Gln Val Tyr Ala
1               5                   10                  15

<210> SEQ ID NO 52
<211> LENGTH: 6
<212> TYPE: PRT
<213> ORGANISM: Artificial Sequence
<220> FEATURE:
<223> OTHER INFORMATION: peptide of consensus V2 region of HIV-1 subtype
      CRF01_AE

<400> SEQUENCE: 52

Lys Leu Asp Ile Val Gln
1               5

<210> SEQ ID NO 53
<211> LENGTH: 9
<212> TYPE: PRT
<213> ORGANISM: Artificial Sequence
<220> FEATURE:
<223> OTHER INFORMATION: peptide of consensus V2 region of HIV-1 subtype
      CRF01_AE

<400> SEQUENCE: 53

Leu Phe Tyr Lys Leu Asp Ile Val Gln
1               5

<210> SEQ ID NO 54
<211> LENGTH: 12
<212> TYPE: PRT
<213> ORGANISM: Artificial Sequence
<220> FEATURE:
<223> OTHER INFORMATION: peptide of consensus V2 region of HIV-1 subtype
      CRF01_AE

<400> SEQUENCE: 54

Val Tyr Ala Leu Phe Tyr Lys Leu Asp Ile Val Gln
1               5                   10

<210> SEQ ID NO 55
<211> LENGTH: 15
<212> TYPE: PRT
<213> ORGANISM: Artificial Sequence
```

```
<220> FEATURE:
<223> OTHER INFORMATION: peptide of consensus V2 region of HIV-1 subtype
      CRF01_AE

<400> SEQUENCE: 55

Lys Gln Lys Val Tyr Ala Leu Phe Tyr Lys Leu Asp Ile Val Gln
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: peptide of consensus V2 region of HIV-1 subtype
      CRF01_AE

<400> SEQUENCE: 56

Arg Asp Lys Lys Gln Lys Val Tyr Ala Leu Phe Tyr Lys Leu Asp
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: peptide of consensus V2 region of HIV-1 subtype
      CRF01_AE

<400> SEQUENCE: 57

Thr Glu Leu Arg Asp Lys Lys Gln Lys Val Tyr Ala Leu Phe Tyr
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: peptide of consensus V2 region of HIV-1 subtype
      CRF01_AE

<400> SEQUENCE: 58

Asn Met Thr Thr Glu Leu Arg Asp Lys Lys Gln Lys Val Tyr Ala
1               5                   10                  15

<210> SEQ ID NO 59
<211> LENGTH: 6
<212> TYPE: PRT
<213> ORGANISM: Artificial Sequence
<220> FEATURE:
<223> OTHER INFORMATION: peptide of consensus V2 region of HIV-1 subtype
      CRF02_AG

<400> SEQUENCE: 59

Arg Leu Asp Val Val Gln
1               5

<210> SEQ ID NO 60
<211> LENGTH: 9
<212> TYPE: PRT
<213> ORGANISM: Artificial Sequence
<220> FEATURE:
<223> OTHER INFORMATION: peptide of consensus V2 region of HIV-1 subtype
      CRF02_AG

<400> SEQUENCE: 60

Leu Phe Tyr Arg Leu Asp Val Val Gln
1               5
```

<210> SEQ ID NO 61
<211> LENGTH: 12
<212> TYPE: PRT
<213> ORGANISM: Artificial Sequence
<220> FEATURE:
<223> OTHER INFORMATION: peptide of consensus V2 region of HIV-1 subtype
      CRF02_AG

<400> SEQUENCE: 61

Val Tyr Ala Leu Phe Tyr Arg Leu Asp Val Val Gln
1               5                   10

<210> SEQ ID NO 62
<211> LENGTH: 15
<212> TYPE: PRT
<213> ORGANISM: Artificial Sequence
<220> FEATURE:
<223> OTHER INFORMATION: peptide of consensus V2 region of HIV-1 subtype
      CRF02_AG

<400> SEQUENCE: 62

Lys Gln Lys Val Tyr Ala Leu Phe Tyr Arg Leu Asp Val Val Gln
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: peptide of consensus V2 region of HIV-1 subtype
      CRF02_AG

<400> SEQUENCE: 63

Arg Asp Lys Lys Gln Lys Val Tyr Ala Leu Phe Tyr Arg Leu Asp
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: peptide of consensus V2 region of HIV-1 subtype
      CRF02_AG

<400> SEQUENCE: 64

Thr Glu Leu Arg Asp Lys Lys Gln Lys Val Tyr Ala Leu Phe Tyr
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: peptide of consensus V2 region of HIV-1 subtype
      CRF02_AG

<400> SEQUENCE: 65

Asn Met Thr Thr Glu Leu Arg Asp Lys Lys Gln Lys Val Tyr Ala
1               5                   10                  15

<210> SEQ ID NO 66
<211> LENGTH: 42
<212> TYPE: PRT
<213> ORGANISM: Artificial Sequence
<220> FEATURE:
<223> OTHER INFORMATION: peptide V2 sequence in the recombinant ALVAC
      priming immunogen -continued

```
<400> SEQUENCE: 66

Cys Ser Phe Asn Met Thr Thr Glu Leu Arg Asp Lys Lys Gln Lys Val
1               5                   10                  15

His Ala Leu Phe Tyr Lys Leu Asp Ile Val Pro Ile Glu Asp Asn Thr
            20                  25                  30

Ser Ser Ser Glu Tyr Arg Leu Ile Asn Cys
        35                  40

<210> SEQ ID NO 67
<211> LENGTH: 42
<212> TYPE: PRT
<213> ORGANISM: Artificial Sequence
<220> FEATURE:
<223> OTHER INFORMATION: peptide V2 sequence in the protein boosting
      gp120 immunogen AIDSVAX E

<400> SEQUENCE: 67

Cys Ser Phe Asn Met Thr Thr Glu Leu Arg Asp Lys Lys Gln Lys Val
1               5                   10                  15

His Ala Leu Phe Tyr Lys Leu Asp Ile Val Pro Ile Glu Asp Asn Asn
            20                  25                  30

Asp Ser Ser Glu Tyr Arg Leu Ile Asn Cys
        35                  40

<210> SEQ ID NO 68
<211> LENGTH: 40
<212> TYPE: PRT
<213> ORGANISM: Artificial Sequence
<220> FEATURE:
<223> OTHER INFORMATION: peptide V2 sequence in the protein boosting
      gp120 immunogen AIDSVAX B

<400> SEQUENCE: 68

Cys Ser Phe Asn Ile Thr Thr Ser Ile Gly Asp Lys Met Gln Lys Glu
1               5                   10                  15

Tyr Ala Leu Leu Tyr Lys Leu Asp Ile Glu Pro Ile Asp Asn Asp Ser
            20                  25                  30

Thr Ser Tyr Arg Leu Ile Ser Cys
        35                  40

<210> SEQ ID NO 69
<211> LENGTH: 42
<212> TYPE: PRT
<213> ORGANISM: Artificial Sequence
<220> FEATURE:
<223> OTHER INFORMATION: peptide of cyclic V2 scrambled crown

<400> SEQUENCE: 69

Cys Ser Phe Asn Met Thr Thr Glu Leu Arg Asp Lys Gln Val Leu Phe
1               5                   10                  15

Lys Asp Ile His Lys Ile Val Lys Pro Leu Tyr Ala Glu Asp Asn Thr
            20                  25                  30

Ser Ser Ser Glu Tyr Arg Leu Ile Asn Cys
        35                  40

<210> SEQ ID NO 70
<211> LENGTH: 42
<212> TYPE: PRT
<213> ORGANISM: Artificial Sequence
<220> FEATURE:
<223> OTHER INFORMATION: peptide of cyclic V2 scrambled flanks

<400> SEQUENCE: 70
```

```
Cys Glu Asn Leu Thr Asp Lys Met Phe Thr Ser Arg Lys Gln Lys Val
1               5                   10                  15

His Ala Leu Phe Tyr Lys Leu Asp Ile Val Pro Ile Ser Glu Ser Arg
            20                  25                  30

Leu Asp Glu Thr Asn Tyr Asn Ile Ser Cys
        35                  40

<210> SEQ ID NO 71
<211> LENGTH: 82
<212> TYPE: PRT
<213> ORGANISM: Artificial Sequence
<220> FEATURE:
<223> OTHER INFORMATION: peptide of gp70-V1V2 from subtype B case A2

<400> SEQUENCE: 71

Cys Val Thr Leu Asn Cys Ile Asp Leu Arg Asn Ala Thr Asn Ala Thr
1               5                   10                  15

Ser Asn Ser Asn Thr Thr Asn Thr Thr Ser Ser Ser Gly Gly Leu Met
            20                  25                  30

Met Glu Gln Gly Glu Ile Lys Asn Cys Ser Phe Asn Ile Thr Thr Ser
        35                  40                  45

Ile Arg Asp Lys Val Gln Lys Glu Tyr Ala Leu Phe Tyr Lys Leu Asp
    50                  55                  60

Ile Val Pro Ile Asp Asn Pro Lys Asn Ser Thr Asn Tyr Arg Leu Ile
65                  70                  75                  80

Ser Cys

<210> SEQ ID NO 72
<211> LENGTH: 19
<212> TYPE: PRT
<213> ORGANISM: Artificial Sequence
<220> FEATURE:
<223> OTHER INFORMATION: peptide of V2 A244-92TH023

<400> SEQUENCE: 72

Asn Met Thr Thr Glu Leu Arg Asp Lys Lys Gln Lys Val His Ala Leu
1               5                   10                  15

Phe Tyr Lys

<210> SEQ ID NO 73
<211> LENGTH: 23
<212> TYPE: PRT
<213> ORGANISM: Artificial Sequence
<220> FEATURE:
<223> OTHER INFORMATION: peptide of V2 MN

<400> SEQUENCE: 73

Ile Thr Thr Ser Ile Gly Asp Lys Met Gln Lys Glu Tyr Ala Leu Leu
1               5                   10                  15

Tyr Lys Leu Asp Ile Glu Pro
            20

<210> SEQ ID NO 74
<211> LENGTH: 21
<212> TYPE: PRT
<213> ORGANISM: Artificial Sequence
<220> FEATURE:
<223> OTHER INFORMATION: peptide of V2 K178

<400> SEQUENCE: 74

Lys Lys Lys Val His Ala Leu Phe Tyr Lys Leu Asp Ile Val Pro Ile
```

```
1               5               10              15
Glu Asp Lys Lys Lys
                20

<210> SEQ ID NO 75
<211> LENGTH: 7
<212> TYPE: PRT
<213> ORGANISM: Artificial Sequence
<220> FEATURE:
<223> OTHER INFORMATION: peptide of cathepsin D cleavage site from V2 of
      MN

<400> SEQUENCE: 75

Gln Lys Glu Tyr Ala Leu Leu
1               5

<210> SEQ ID NO 76
<211> LENGTH: 7
<212> TYPE: PRT
<213> ORGANISM: Artificial Sequence
<220> FEATURE:
<223> OTHER INFORMATION: peptide of V2 of A244

<400> SEQUENCE: 76

Gln Lys Val His Ala Leu Phe
1               5
```